United States Patent
Lee et al.

(10) Patent No.: US 10,653,359 B2
(45) Date of Patent: May 19, 2020

(54) SYSTEM AND METHOD FOR PROVIDING WALKING PATH GUIDANCE SERVICE BASED ON MEASUREMENT OF MOTION OF USER

(71) Applicant: SK PLANET CO., LTD., Seongnam-si, Gyeonggi-do (KR)

(72) Inventors: Kwonho Lee, Pyeongtak-si (KR); Seulmaro Jeon, Seongnam-si (KR)

(73) Assignee: SK PLANET CO., LTD., Seongnam-si, Gyeonggi-do (KR)

( * ) Notice: Subject to any disclaimer, the term of this patent is extended or adjusted under 35 U.S.C. 154(b) by 137 days.

(21) Appl. No.: 15/913,697

(22) Filed: Mar. 6, 2018

(65) Prior Publication Data

US 2018/0192949 A1    Jul. 12, 2018

Related U.S. Application Data

(63) Continuation of application No. 15/298,229, filed on Oct. 20, 2016, now Pat. No. 9,943,262.

(30) Foreign Application Priority Data

| Oct. 26, 2015 | (KR) | .................. 10-2015-0148972 |
| Oct. 27, 2015 | (KR) | .................. 10-2015-0149615 |
| Oct. 30, 2015 | (KR) | .................. 10-2015-0152491 |

(51) Int. Cl.
  *A61B 5/00*   (2006.01)
  *A61B 5/11*   (2006.01)
  (Continued)

(52) U.S. Cl.
  CPC .......... *A61B 5/6803* (2013.01); *A61B 5/0002* (2013.01); *A61B 5/0022* (2013.01); *A61B 5/1112* (2013.01); *A61B 5/486* (2013.01); *A61B 5/7246* (2013.01); *G01C 21/20* (2013.01); *G06Q 30/0207* (2013.01); *G06Q 30/0261* (2013.01); *G06Q 30/0267* (2013.01);
  (Continued)

(58) Field of Classification Search
  CPC ...... A61B 5/6803; A61B 5/486; G01C 21/20; G06Q 30/0641
  See application file for complete search history.

(56) References Cited

U.S. PATENT DOCUMENTS

| 6,574,549 B2 | 6/2003 | Cato et al. |
| 9,677,901 B2 | 6/2017 | Yamamoto |

(Continued)

FOREIGN PATENT DOCUMENTS

| KR | 2012-0001925 A | 1/2012 |

*Primary Examiner* — Michael J Zanelli
(74) *Attorney, Agent, or Firm* — Fenwick & West LLP

(57) ABSTRACT

The present invention relates to a system and method for providing a walking path guidance service based on measurement of a motion of a user, and there is provided a device for providing a walking path guidance service, the device including: a sensor unit for measuring a motion and position information of a user; a reference information creation unit for calculating an average walking speed using the measured motion and position information of the user; and a walking path guidance unit for creating a walking path from a starting point to a destination and calculating a time of arrival at the destination of the walking path according to the average walking speed.

17 Claims, 26 Drawing Sheets

(51) Int. Cl.
*G01C 21/20* (2006.01)
*G06Q 30/02* (2012.01)
*G16H 40/67* (2018.01)

(52) U.S. Cl.
CPC ......... *G06Q 30/0269* (2013.01); *G16H 40/67* (2018.01); *A61B 2503/12* (2013.01)

(56) References Cited

U.S. PATENT DOCUMENTS

| | | |
|---|---|---|
| 2011/0193985 A1 | 8/2011 | Inoue |
| 2014/0006310 A1 | 1/2014 | Hamilton, II et al. |
| 2014/0267399 A1 | 9/2014 | Lamer |
| 2014/0358439 A1 | 12/2014 | Jamain et al. |
| 2015/0039461 A1 | 2/2015 | Gadre et al. |
| 2015/0186982 A1 | 7/2015 | Higgins et al. |
| 2015/0204670 A1 | 7/2015 | Morrison et al. |
| 2015/0294389 A1 | 10/2015 | Jones et al. |
| 2016/0025499 A1 | 1/2016 | Moore et al. |
| 2016/0078512 A1 | 3/2016 | Yopp et al. |
| 2016/0104232 A1* | 4/2016 | Perks ................ G06Q 30/0631 705/26.62 |

* cited by examiner

SYSTEM AND METHOD FOR PROVIDING WALKING PATH GUIDANCE SERVICE BASED ON MEASUREMENT OF MOTION OF USER

CROSS REFERENCE TO RELATED APPLICATIONS

The present application is a continuation application of U.S. patent application Ser. No. 15/298,229, filed Oct. 20, 2016, which claims the benefit of Korean Patent Application No. 10-2015-0148972 filed in the Korean Intellectual Property Office on Oct. 26, 2015, Korean Patent Application No. 10-2015-0149615 filed in the Korean Intellectual Property Office on Oct. 27, 2015 and Korean Patent Application No. 10-2015-0152491 filed in the Korean Intellectual Property Office on Oct. 30, 2015, the entire contents of which are incorporated herein by reference.

BACKGROUND OF THE INVENTION

Field of the Invention

The present invention relates to a system and method for providing a walking path guidance service based on measurement of a motion of a user, and more specifically, to a system and method for providing a walking path guidance service based on measurement of a motion of a user, which measures a motion and position information of the user using a smart device, calculates an average walking speed using the measured motion and position information, creates a walking path from a starting point to a destination when the destination is input, and calculates a time of arrival at the destination by the average walking speed of the walking path.

Background of the Related Art

A wearable devices is literally a device that can be worn on a human body, and there are various kinds of wearable devices according to wearing portions, such as glasses, a watch, shoes, a ring, a belt, a band, a necklace, a headset, clothes and the like. Such wearable devices are currently in a rapidly distributed stage, and among them, wearable glasses, wearable watches and wearable bands closely related to human life and, at the same time, easy to wear form largest product groups.

On the other hand, the wearable device is also referred to as a smart device in other words. It is since that although initiation of operation by an input of a user is needed, if once the operation is initiated, various additional information can be automatically created and provided to the user thereafter. For example, if a user wearing a wearable watch desires to measure his or her heart rate, the wearable watch measures the heart rate of the user as soon as the user presses a heart rate measurement input button and creates and provides various information to the user based on the measured heart rate. Meanwhile, a lot of wearable devices which do not need initiation of operation by an input of a user also appear recently. For example, a wearable band may continuously measure a heart rate of a user although there is no initiation of operation by an input of a user, and it is highly probable that wearable devices of the future will be developed in a direction that does not need initiation of operation by an input of a user. It is since that convenience of operating a device will be increased as the input of a user is not needed.

The source of various additional information provided by the wearable device to a user is information measured from the user. Accordingly, the wearable device should necessarily install sensors for measuring various information from the user, and the more the kinds of installed sensors, the more information can be measured from the user. Accordingly, recent wearable devices tend to necessarily install a heart rate measurement sensor, a global positioning system (GPS) sensor and a walking count measurement sensor, and studies for installing various kinds of sensors in the limited inner space of the device are continued.

After measuring the information from the user through the installed sensors, the wearable device may create various additional information based on the information and provide the user with the information. For example, the wearable device may measure the current position of the user and provide information on nearby stores or products related to the interest of the user. Although the additional information can be provided through a function of the wearable device itself, since all the additional information needed for different users cannot be provided through one wearable device, applications installed in the wearable device are developed together recently. Here, an application can be regarded as a kind of application program and may perform a function of creating and providing various additional information based on the information measured through a function of the wearable device itself. In the above example, all the information about nearby stores or products related to the interest of the user can be provided by the application. That is, whenever a new application is developed, additional information that can be provided to the user through the wearable device is diversified, and thus development of applications can be regarded as a companion to go forward together with development of the wearable device itself.

Meanwhile, construction of a system capable of making a payment through a wearable device emerges as a main issue in the related industries recently. For example, although a user does not to take out his or her wallet and make a payment, the user may make a payment through a wearable device by installing a near field communication (NFC) function in the wearable device itself and registering a credit card of the user in an application. That is, the wearable device may perform a mobile wallet function on behalf of conventional wallets. However, since there are a lot of problems related to security, such as personal information of a user, approval of card payment and the like, there are a lot of technical problems to be solved.

In addition, a service system for measuring a motion of a user using a wearable device and providing a walking pattern using information on the measured motion has already been constructed. However, a service for providing an estimated time of arrival at a destination according to an average walking speed of a user is not provided yet in the prior art.

SUMMARY OF THE INVENTION

The present invention is to propose a service for providing an estimated time of arrival at a destination according to an average walking speed of a user using a wearable device.

An object of the present invention is to provide a system and method for providing a walking path guidance service based on measurement of a motion of a user, which provides an estimated time of arrival at a destination according to an average walking speed of the user using a wearable device.

Another object of the present invention is to provide a navigation service using information on the current position and dropped-in products so that a wearable device of a user may move from the current position of the user to a place where an interested product is placed.

Another object of the present invention is to provide a service associated with digital contents in real-time using navigation information.

Still another object of the present invention is to provide an optimum moving path to a current navigation service user by utilizing attribute information of products to be purchased by navigation service users.

Still another object of the present invention is to provide a shortest moving path using locations of products to be purchased by navigation service users.

The present invention has been made to solve the problems described above, and an object of the present invention is to provide a navigation service using images photographed by a wearable device of a user while moving to a destination and information related thereto.

Another object of the present invention is to provide a service associated with digital contents in real-time using navigation information.

Still another object of the present invention is to provide an optimum moving path to a current navigation service user by using moving paths to a store to visit and photographed images provided by navigation service users or information on the images.

Still another object of the present invention is to provide a moving path which can provide marketing information to the current navigation service user using the preference, of a service provider providing a navigation service, for the user.

Still another object of the present invention is to provide a system and method for providing a walking path guidance service based on measurement of a motion of a user, which can recommend a taxi call service if the moving speed of the user is lower than a predetermined speed or too slow.

DESCRIPTION OF SYMBOLS

Figure 1:
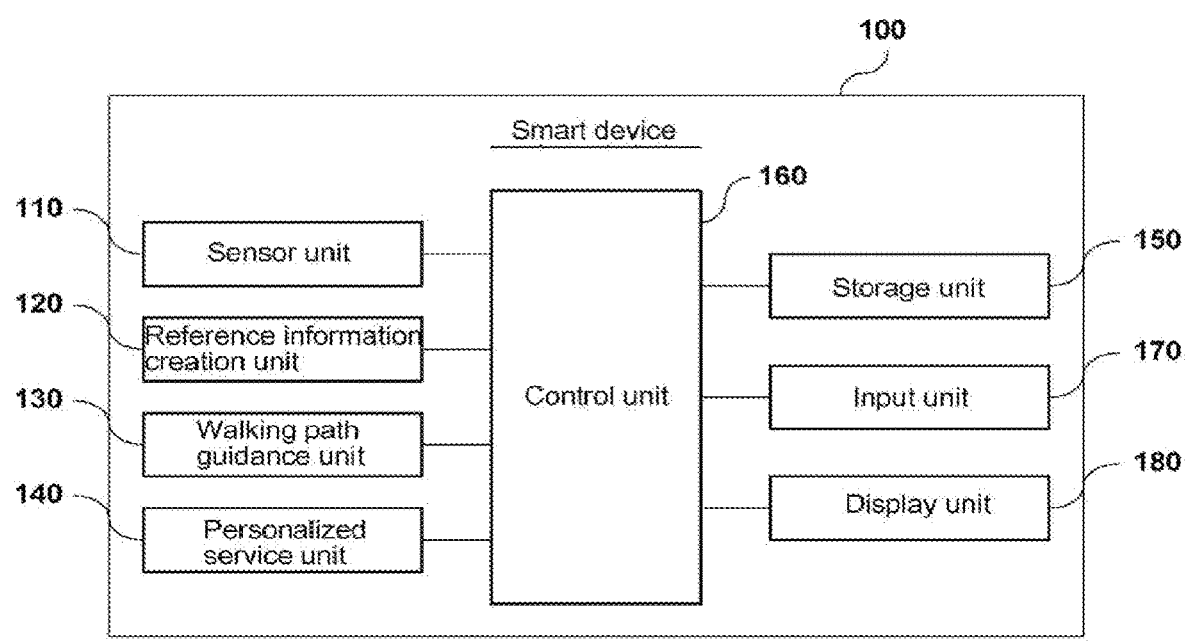
FIG. 1 is a block diagram schematically showing the configuration of a smart device for providing a walking path guidance service based on measurement of a motion of a user according to an embodiment of the present invention.

100: Smart device
110: Sensor unit
120: Reference information creation unit
130: Walking path guidance unit
140: Personalized service unit
150, 250: Storage unit
160: Control unit 170: Input unit
180: Display unit
200: Service server
210: Communication unit
220: Database
230: Walking path service unit
240: Recommendation unit
100': Wearable device
110': Interested product storage unit
120': User position confirmation unit
130': Data transmission unit
140': Data reception unit
150': Display unit
200': Navigation service providing device
210': Data reception unit
220': Product information database
230': Navigation information providing module
231': Interested product information extraction unit
232': Shortest distance navigation information creation unit
233': Product attribute navigation information creation unit
234': Navigation information selection unit
240': Data transmission unit
300': Contents providing server
310': Navigation information reception unit
320': Digital contents providing unit
330': Digital contents transmission unit
400': Membership connection device
410': Membership holder authentication performing unit
420': Membership information transmission unit
430': Membership acquisition request transmission unit
440': Membership acquisition approval message reception unit
100": Wearable device
110": Camera module
120": History storage unit
130": Information transmission unit
140": Data reception unit
150": Display unit
200": Navigation service providing device
210": Navigation information database
220": Navigation information providing module
221": Distance measurement unit
222": Digital contents provider preference determination unit
223": Navigation information selection unit
230": Data transmission unit
300": Contents providing server
310": Navigation information reception unit
320": Digital contents providing unit
330": Digital contents transmission unit
400": Membership connection device
410": Membership holder authentication performing unit
420": Membership information transmission unit
430": Membership acquisition request transmission unit
440": Membership acquisition approval message reception unit

DETAILED DESCRIPTION OF THE PREFERRED EMBODIMENT

Hereinafter, a 'system and method for providing a walking path guidance service based on measurement of a motion of a user' according to the present invention will be described in detail with reference to the accompanying drawings. The disclosed embodiments are provided to enable those skilled in the art to easily understand the scope of the present invention, and the present invention is not limited by such embodiments. Moreover, matters illustrated in the drawings are schematized in order to describe or explain the embodiments of the present invention more easily and hence may be different from actually embodied forms.

Meanwhile, the constitutional components expressed below are merely examples for implementing the present invention. Accordingly, other constitutional components may be used in other implementations of the present invention without departing from the spirit and scope of the present invention.

In addition, although each constitutional component may be implemented only in a pure hardware or software configuration, it also can be implemented by combining various hardware or software configurations performing the same function. In addition, two or more constitutional components may be implemented together by one piece of hardware or software.

In addition, the expression of 'including' a component is an expression of an 'open type' which merely refers to existence of a corresponding component, and it should not be construed as precluding additional components.

FIG. 1 is a block diagram schematically showing the configuration of a device for providing a walking path guidance service based on measurement of a motion of a user according to an embodiment of the present invention. In the embodiment, the device for providing a walking path guidance service may be a smart phone. Hereinafter, although a case of using a smart device as a device for providing a walking path guidance service is described as an example, the device for providing a walking path guidance service according to the present invention is not limited to the smart device.

Referring to FIG. 1, a smart device 100 for providing a walking path guidance service based on measurement of a motion of a user may include a sensor unit 110, a reference information creation unit 120, a walking path guidance unit 130, a storage unit 150 and a control unit 160. In an embodiment, the smart device 100 may further include a personalized service unit 140.

The sensor unit 110 is installed in the smart device 100 and measures a motion or biometric information of a user. Here, the biometric information may include a pulse rate, a blood pressure, blood sugar, blood oxygen saturation (SpO2) and the like.

The sensor unit 110 is a configuration for measuring a motion according to walking of a user and may be a motion sensing sensor. The motion sensing sensor is a sensor for measuring a motion of the feet of a user and may include, for example, an acceleration sensor and the like. The acceleration sensor may sense a motion of a user using a three-axis acceleration sensor axis. The acceleration sensor measures magnitude of acceleration according to a motion of the user. The acceleration sensor measures a degree of acceleration using a physical displacement of a mechanical device configured inside thereof and outputs the degree of acceleration as a frequency or a voltage. For example, the acceleration sensor may follow one of the methods including an inertial type, a gyro type and a silicon type.

The sensor unit 110 may measure biometric information of a user. In this case, the sensor unit 110 senses and converts basic physical properties such as current, voltage, resistance and the like containing biometric measurement information into a data of a desired form. The sensor unit 110 includes corresponding measurement sensors according to the types of measurement objects desired to be measured, such as a pulse rate sensor, a blood pressure sensor, a blood sugar sensor and the like. Since the sensor unit 110 periodically or continuously senses the measured biometric information and transmits an electrical signal corresponding thereto to the control unit in the main body, the user may confirm a result through the smart device 100 or a user terminal or the like connected to the smart device 100, and, in an emergency situation, the user terminal connected to the smart device 100 may directly inform the result to the outside on behalf of the user.

In addition, the sensor unit 110 measures position information, in addition to motion and biometric information of the user. A position sensing sensor is a sensor for measuring the current position of a user and may include, for example, a GPS sensor or the like.

The reference information creation unit 120 calculates an average walking speed using the motion and position information measured by the sensor unit 110. Since the current position of the smart device 100 can be grasped in real-time, the average walking speed can be easily grasped by calculating the moving time and moving distance or through various other methods.

The reference information creation unit 120 calculates an average walking speed of the user using the motion and position information measured by the sensor unit 110. That is, the reference information creation unit 120 detects steps using a motion measurement value of the sensor unit 110. At this point, the reference information creation unit 120 may use a peak value detection method, a preset section detection method, a zero-cross detection method or the like to detect the steps. If the zero-cross detection method is used, the smart device 100 recognizes a moment when a signal passes through a zero point as a step after signal-processing a raw signal of an accelerometer using sliding window summing and signal difference.

Then, the reference information creation unit 120 calculates a moving distance of the user using the position information measured by the sensor unit 110 and analyzes an average number of steps according to the moving distance as a walking pattern. Then, the reference information creation unit 120 obtains an average walking speed by dividing the moving distance by the moving time (average walking speed=moving distance/moving time). At this point, if it is set to measure the speed every few steps, the moving distance is a sum of the strides corresponding to the number of steps, and the moving time a total time taken to complete the walk. If it is set to measure the speed every few seconds, the moving distance is a sum of strides corresponding to the number of steps made within the time, and the set time is the moving time. Then, the moving speed is obtained by dividing the moving distance obtained by the sum of the values of strides as many as the set number of steps by the time taken to move as many as the set number of steps, or if it is set to measure the speed by the time, not the number of steps, the moving speed is obtained by dividing the moving distance obtained as a sum of the values of strides corresponding to the number of steps made as much as the set time by the set time.

The walking path guidance unit 130 creates a walking path from a starting point to a destination and calculates a time of arrival at the destination by the average walking speed of the walking path.

That is, the walking path guidance unit 130 receives a starting point and a destination form the user. If the current position is known by the sensor unit 110, the walking path guidance unit 130 searches for a walking path using the current position as a starting point instead of receiving the starting point. At this point, the searched walking path may be a shortest walking path from the starting point to the destination.

Hereinafter, a method of creating a walking path by the walking path guidance unit 130 will be described. As a first method, the walking path guidance unit 130 receives a starting point and a destination and creates a walking path, and if there is a reduced path passing through the inside of a building among the paths created between the starting point and the destination, the walking path guidance unit 130 may create the corresponding reduced path as a walking path. At this point, the walking path guidance unit 130 stores and manages even the indoor moving path inside the building together with road information. The walking path guidance unit 130 may search for coordinate information of the starting point and the destination, map image information of corresponding coordinates and scale information from the map information stored in the storage unit 150 and create a walking path mainly focused on roads. That is, the walking path guidance unit 130 creates path information mainly focused on roads according to the starting point and the destination and determines whether or not a building which stores an indoor moving path is included in the created path. If there is an indoor moving path as a result of the determination, the walking path guidance unit 130 creates path information including the indoor moving path. Like this, the walking path guidance unit 130 creates at least one or more pieces of path information including the walking path mainly focused on roads and the indoor moving path.

As a second method, the walking path guidance unit 130 creates an optimum walking path considering the number of waiting sections in the walking path and the moving distance between the starting point and the destination. The walking path guidance unit 130 may grasp at least one or more walking paths between the starting point and the destination and create, among the grasped walking paths, a walking path consuming the shortest time as an optimum walking path based on the moving distance and the number of waiting sections including crosswalks.

If a walking path from the starting point to the destination is created in a method as described above, the walking path guidance unit 130 calculates a time required to move to the destination, i.e., an arrival time, of each walking path according to the average walking speed created by the reference information creation unit 120. Then, the walking path guidance unit 130 outputs walking path information including a walking path and an arrival time.

Therefore, the user may be provided with the path information focused on the road, the indoor moving path, the shortest distance moving path and the like and provided with information on a time required, a moving distance, information on entrances and exits of a building to drop in and the like of each path to pass through by confirming the walking path information, walking information and the like through the smart device 100.

The walking path guidance unit 130 displays the walking path from the starting point to the destination on an electronic map. The walking path displayed on the electronic map may be displayed as a shortest walking path among the walking paths from the starting point to the destination. At this point, when the user moves along the walking path, the walking path guidance unit 130 starts to move an identifier, indicating movement of the user on the walking path of the electronic map, at a preset speed. Like this, since an identifier indicating movement of the user is moved on the walking path of the electronic map, the user may approximately confirm a point where the user is currently positioned even while walking.

In addition, the walking path guidance unit 130 may compare the average walking speed created by the reference information creation unit 120 with the current walking speed of the user and output a difference between the average walking speed and the current walking speed through a visual or aural means. If the walking speed of the user is lower than the average walking speed, the walking path guidance unit 130 informs the user that the walking speed of the user is lower than the average walking speed, and in an opposite case, it informs that the walking speed of the user is higher than the average walking speed. At this point, the walking path guidance unit 130 may use a method of an alarm sound, vibration or the like as a method of informing the user of the low or high walking speed, and, for example, the alarm sound or a vibration type of a case when the user should walk slowly is different from the alarm sound or a vibration type of a case when the user should walk fast so that the user may recognize without separately confirming them. If the user adjusts the walking speed to correspond to the average walking speed, the alarm sound or the vibration is stopped so that the user may know that the current speed is a recommended speed.

Since the user is within a range of the average walking speed, the walking path guidance unit 130 may display the current speed together with a message informing to maintain the current speed. That is, if the walking speed of the user is higher than the average walking speed, the walking path guidance unit 130 displays the current walking speed together with a message informing to reduce the walking speed. In addition, the walking path guidance unit 130 also displays the average walking speed. If the walking speed of the user is lower than the average walking speed, the walking path guidance unit 130 displays the current walking speed together with a message informing to increase the walking speed. In addition, the walking path guidance unit 130 also displays the average walking speed.

When a movement according to the walking path of the user is sensed, the personalized service unit 140 calculates a moving speed using the movement measured by the sensor unit 110 and recommends a taxi call service if the calculated moving speed is lower than a preset threshold speed. If the user desires to use the taxi call service, the personalized service unit 140 may search for an unoccupied taxi in the nearest distance from the current position measured by the sensor unit 110 and provide taxi reservation information including the license plate number, an estimated arrival time and the like of the searched unoccupied taxi.

In addition, if the moving speed calculated by using a movement measured by the sensor unit 110 is lower than the preset threshold speed, the personalized service unit 140 determines whether or not the user is in a normal condition by comparing the biometric information of the user measured by the sensor unit 110 with previously stored reference biometric information and outputs abnormal information if the user is in an abnormal condition. At this point, the personalized service unit 140 determines whether or not the user is in a dangerous situation and informs the dangerous situation by way of preset contact information, an emergency contact network or the like if the user is in a dangerous situation.

Meanwhile, the reference information creation unit 120, the walking path guidance unit 130 and the personalized service unit 140 can be implemented by a processor or the like needed to execute a computer program on a computing device. Like this, each of the reference information creation unit 120, the walking path guidance unit 130 and the personalized service unit 140 can be implemented by a physically independent individual configuration or implemented as a form functionally separated within a processor.

The storage unit 150 is a configuration for storing data related to operation of the smart device 100. Here, the storage unit 150 may use a publicized storage medium and may use one or more of publicized storage media such as ROM, PROM, EPROM, EEPROM, RAM and the like.

Particularly, the biometric information measured by the sensor unit 110, a health state related to the biometric information, the average walking speed calculated by the reference information creation unit 120, the walking path created by the walking path guidance unit 130 and the like are stored in the storage unit 150. In addition, map information including map image information, scale information, coordinate information and the like is stored in the storage unit 150. Here, the map information may include indoor moving paths or the like which move from a road to a road.

In addition, a walking path guidance program for providing a walking path guidance service provided by the smart device 100 is stored in the storage unit 150. Electronic map data related to the map information of each area is stored in the storage unit 150. Any file format is allowed as far as the electronic map may display a walking path.

Therefore, the control unit 160 may provide the walking path guidance service provided by the smart device 100 by executing the walking path guidance program stored in the storage unit 150 according to selection of a user.

In addition, an application (or an applet) or the like capable of calculating an average walking speed according to a motion of a user and performing walking path guidance can be stored in the storage unit 150, and the stored information can be selected by the control unit 160 as needed.

The control unit 160 may store an application (or an applet) capable of calculating an average walking speed according to a motion of a user and performing walking path guidance in the storage unit 150 and control to output a walking path by driving the application.

The control unit 160 is a configuration for controlling operation of various constitutional components of the smart device 100, including the sensor unit 110, the reference information creation unit 120, the walking path guidance unit 130, the personalized service unit 140 and the storage unit 150.

The control unit 160 may include at least one arithmetic unit, and, here, the arithmetic unit may be a general-purpose central processing unit (CPU), a programmable device element (CPLD or FPGA) implemented to be suitable for a specific purpose, an application specific integrated circuit (ASIC) or a microcontroller chip.

The smart device 100 according to the present invention may further includes an input unit 170 for receiving information from a user. The input unit 170 can be utilized to receive, particularly, a starting point, a destination and the like. Meanwhile, the input unit 170 can be implemented as an input device such as a keypad, a touch panel or the like and also can be implemented as various input devices other than these input devices. In addition, the input unit 170 can be implemented in the form of a touch screen integrated with a display unit 180.

In addition, the smart device 100 according to the present invention may further include the display unit 180 for displaying various information related to the operation of the smart device 100. Particularly, the display unit 180 may display various kinds of information such as the biometric information measured by the sensor unit 110, a health state related to the biometric information, a walking path, a time of arrival at the destination and the like. The display unit 180 can be implemented through various display devices including an LCD, an LED and the like.

In addition, the smart device 100 according to the present invention may further include a power supply unit (not shown) for supplying power. In addition, the smart device 100 of the present invention may further include a short-range communication unit (not shown) for performing short-range wireless communication with a user terminal possessed by a user. The short-range communication unit may operate according to various specifications such as Wi-Fi, Bluetooth communication, Zigbee communication, infrared communication (IrDA), Radio Frequency (RF) communication including Ultra High Frequency (UHF) communication and Very High Frequency (VHF) communication, Ultra Wide Band (UWB) communication and the like.

A service application according to the present invention can be installed in the smart device 100 to provide a walking path guidance service according to the present invention. The service application installed in the smart device 100 implements the walking path service through the control unit 160. The service application may be installed when the smart device 100 is released or may be downloaded through a communication network. Alternatively, the service application can be recorded in a separate memory device in the form of a program file and transferred to the smart device 100 by connecting the memory device to the smart device 100.

The smart device 100 implemented as described above means a device that can be worn on a human body, and there are various kinds of wearable devices according to wearing portions, such as glasses, a watch, shoes, a ring, a belt, a band, a necklace, a headset, clothes and the like.

Figure 2:
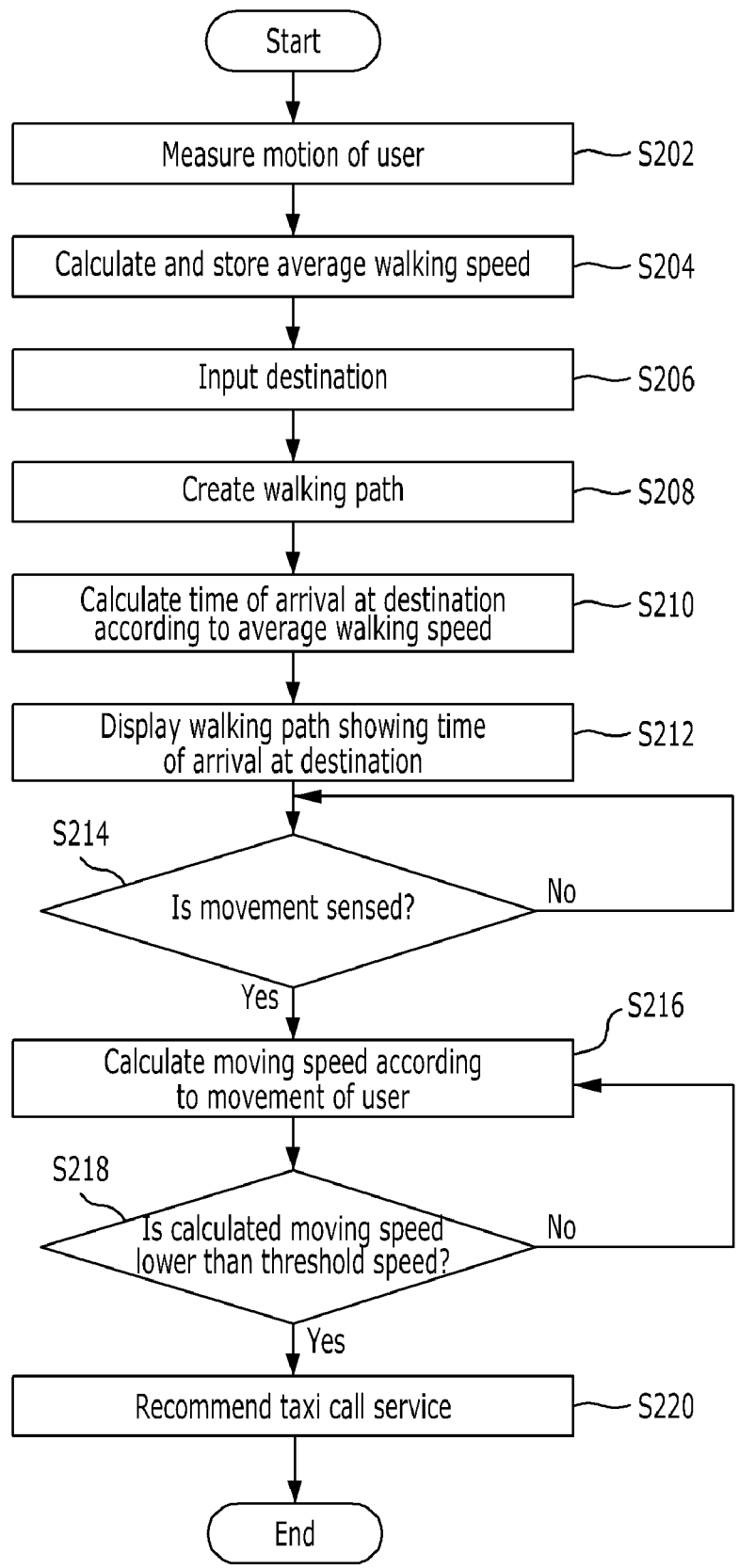
FIG. 2 is a flowchart illustrating a method of providing a walking path guidance service based on measurement of a motion of a user by a smart device according to the present invention.

FIG. 2 is a flowchart illustrating a method of providing a walking path guidance service based on measurement of a motion of a user by a smart device according to the present invention.

Referring to FIG. 2, the smart device measures a motion of a user (step S202) and calculates an average walking speed of the user using the measured motion (step S204). That is, the smart device detects steps using a motion measurement value of the sensor unit, calculates a moving distance of the user using position information, and analyzes an average number of steps according to the moving distance as a walking pattern. Then, the smart device obtains an average walking speed by dividing the moving distance by the moving time (average walking speed=moving distance/moving time).

Thereafter, if a destination is input (step S206), the smart device creates a walking path from a starting point to the destination (step S208). At this point, the smart device receives a starting point and a destination and creates a walking path, and if there is a reduced path passing through the inside of a building among the paths created between the starting point and the destination, the smart device may create the corresponding reduced path as a walking path. In addition, the smart device may create an optimum walking path considering the number of waiting sections in the walking path and the moving distance between the starting point and the destination.

The smart device calculates a time of arrival at the destination of the walking path according to an average walking speed (step S210) and displays the calculated time of arrival at the destination (step S212). At this point, the smart device may display the walking path together with the time of arrival at the destination.

Then, if movement of the user according to the walking path is sensed (step S214), the smart device calculates a moving speed by measuring a motion of the user according to the movement (step S216).

Then, the smart device determines whether or not the calculated moving speed is lower than a preset threshold speed (step S218) and recommends a taxi call service if the calculated moving speed is lower than a preset threshold speed (step S220). If the user desires to use the taxi call service, the smart device may search for an unoccupied taxi in the nearest distance from the current position measured by the sensor unit and provide taxi reservation information including the license plate number, an estimated arrival time and the like of the searched unoccupied taxi.

Figure 3:
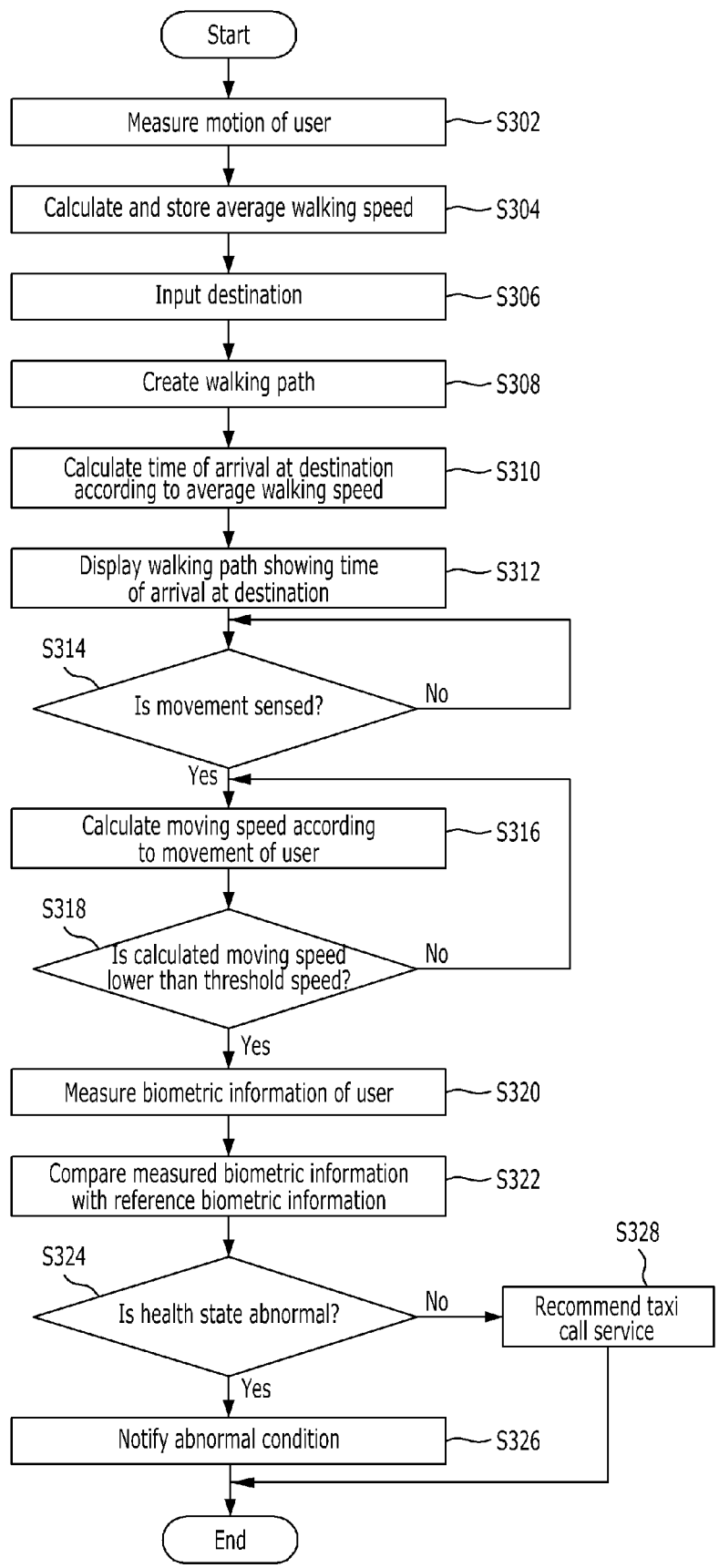
FIG. 3 is a flowchart illustrating a method of providing a walking path guidance service based on measurement of a motion by a smart device according to the present invention.

FIG. 3 is a flowchart illustrating a method of providing a walking path guidance service based on measurement of a motion by a smart device according to the present invention.

Referring to FIG. 3, the smart device measures a motion of a user (step S302) and calculates an average walking speed of the user using the measured motion (step S304).

Thereafter, if a destination is input (step S306), the smart device creates a walking path from a starting point to the destination (step S308).

The smart device calculates a time of arrival at the destination of the walking path according to the average walking speed (step S310) and displays the calculated time of arrival at the destination (step S312). At this point, the smart device may display the walking path together with the time of arrival at the destination.

Then, if movement of the user according to the walking path is sensed (step S314), the smart device calculates a moving speed by measuring a motion of the user according to the movement (step S316).

Then, the smart device determines whether or not the calculated moving speed is lower than a preset threshold speed (step S318).

If the calculated moving speed is lower than the threshold speed as a result of the determination at step S318, the smart device measures biometric information of the user (step S320), compares the measured biometric information with previously stored reference biometric information (step S322), and determines whether or not the user is in a normal condition (step S324).

If the user is in an abnormal condition as a result of the determination at step S324, the smart device outputs abnormal information (step S326), and if the user is not in an abnormal condition, the smart device recommends a taxi call service (step S328). If the biometric information of the user is abnormal, the smart device determines whether or not the user is in a dangerous situation, and if the user is in a dangerous situation, it may inform the dangerous situation by way of preset contact information, an emergency contact network or the like.

Figure 4:
FIG. 4 is a view showing a system for providing a walking path guidance service based on measurement of a motion of a user according to another embodiment of the present invention.

FIG. 4 is a view showing a system for providing a walking path guidance service based on measurement of a motion of a user according to another embodiment of the present invention.

Referring to FIG. 4, the system for providing a walking path guidance service based on measurement of a motion of a user includes a smart device 100 and a service server 200, and these are connected through a communication network.

The smart device 100 calculates an average walking speed by measuring a motion of the user, and if a destination is input, the smart device 100 transmits a walking path information request signal including the average walking speed and the destination to the service server 200 and receives walking path information from the service server 200. That is, the smart device 100 detects steps using a motion measurement value of the sensor unit, calculates a moving distance of the user using the position information measured by the sensor unit and analyzes an average number of steps according to the moving distance as a walking pattern. Then, the smart device 100 obtains an average walking speed by dividing the moving distance by the moving time (average walking speed=moving distance/moving time). If a destination is input, the smart device 100 transmits a walking path information request signal including the average walking speed and the destination to the service server 200.

If movement of the user according to the walking path is sensed, the smart device 100 calculates a moving speed by measuring a motion of the user according to the movement and transmits information on the calculated moving speed to the service server 200. Here, the moving speed information may include a moving speed, smart device identification information and the like.

In addition, if the calculated moving speed is lower than a preset threshold speed, the smart device 100 measures biometric information of the user, determines whether or not the user is in a normal condition by comparing the measured biometric information with previously stored reference biometric information, and outputs abnormal information if the user is in an abnormal condition. At this point, the smart device 100 determines whether or not the user is in a dangerous situation, and if the user is in a dangerous situation, the smart device 100 may inform the dangerous situation by way of preset contact information, an emergency contact network or the like.

The smart device 100 means a device that can be worn on a human body, and there are various kinds of wearable devices according to wearing portions, such as glasses, a watch, shoes, a ring, a belt, a band, a necklace, a headset, clothes and the like.

The smart device 100 used in the present invention is characterized by measuring a motion, a position and biometric information of the user. Here, the biometric information may include a pulse rate, a blood pressure, blood sugar, blood oxygen saturation (SpO2) and the like. At this point, the smart device 100 may measure the biometric information by sensing basic physical properties such as current, voltage, resistance and the like containing biometric measurement information such as a pulse rate, a blood pressure, blood sugar, blood oxygen saturation (SpO2) and the like.

An application (or an applet) capable of calculating a moving speed according to a motion of the user can be stored in the smart device 100, and the smart device 100 may output the walking path information provided by the service server 200 through the application.

A service application according to the present invention can be installed in the smart device 100 in order to provide a walking path guidance service according to the present invention. The service application installed in the smart device 100 implements the walking path service through the control unit 160. The service application may be installed when the smart device 100 is released or may be downloaded through a communication network. Alternatively, the service application can be recorded in a separate memory device in the form of a program file and transferred to the smart device 100 by connecting the memory device to the smart device 100.

If the walking path information request signal is received from the smart device 100, the service server 200 creates a walking path from the starting point to the destination, calculates a time of arrival at the destination by the average walking speed of the walking path, and transmits walking path information including the walking path and the time of arrival at the destination to the smart device 100. Here, the walking path information request signal may include smart device identification information, the starting point, the destination, the average walking speed and the like. The service server receives the starting point and the destination and creates a walking path, and if there is a reduced path passing through the inside of a building among the paths created between the starting point and the destination, the service server may create the corresponding reduced path as a walking path. In addition, the service server may create an optimum walking path considering the number of waiting sections in the walking path and the moving distance between the starting point and the destination. Then, the service server calculates a time of arrival at the destination using the distance and the average walking speed of the walking path.

If the moving speed of the smart device 100 is lower than a preset threshold speed, the service server 200 recommends a taxi call service. If the user desires to use the taxi call service, the service server 200 may search for an unoccupied taxi in the nearest distance from the current position of the user, transmit taxi reservation information including the license plate number, an estimated arrival time and the like of the searched unoccupied taxi to the smart device 100 of the user, and transmit the user's position, user identification information (the phone number, the identification information of the smart device and the like) and the like to the driver of the searched taxi.

Such a service server will be described in detail with reference to FIG. 5.

In the above description, the smart device 100 is provided with a display unit and may display path information, a time of arrival at a destination and the like transmitted from the service server 200. However, the smart device 100 may not be provided with a display unit. In this case, the system for providing a walking path guidance service based on measurement of a motion of a user may further include a user terminal (not shown).

As another embodiment of the present invention, the system for providing a walking path guidance service based on measurement of a motion of a user may further include a user terminal for storing and inputting the biometric information measured by the smart device 100 and the path information, the time of arrival at a destination, the taxi call service and the like received from the service server.

Accordingly, in the present invention, since the user terminal is also connected, as well as the smart device 100 and the service server 200, information on a motion is provided to the user even while the user does not wear the smart device 100, and the user may be provided with a taxi call service from the service server 200.

The smart device 100 may transmit the measured motion information, biometric information and position information to the user terminal (e.g., a smart phone) paired with the smart device 100. For example, the smart device 100 may transmit and receive data using a short-range communication network such as NFC or Bluetooth.

The user terminal includes a Personal Digital Assistant (PDA), a smart phone, a cellular phone, a Personal Communication Service (PCS) phone, a Global System for Mobile (GSM) phone, a Wideband CDMA (W-CDMA) phone, a CDMA-2000 phone, a Mobile Broadband System (MBS) phone and the like which can be applied in a variety of wired and wireless environments. Here, although the user terminal may represent a small portable device, embodiments of the present invention will not be specially limited thereto since the user terminal can be referred to as a mobile communication terminal if the user terminal includes a camcorder, a laptop computer or the like.

Figure 5:
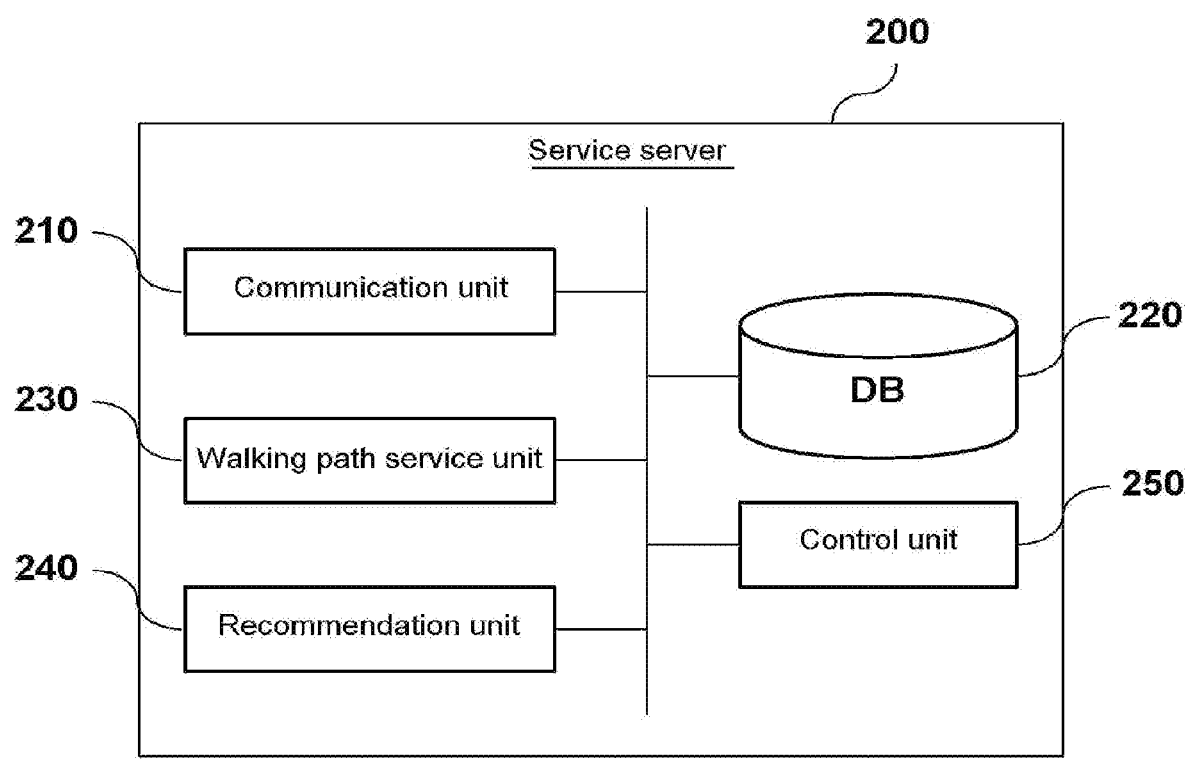
FIG. 5 is a block diagram schematically showing the configuration of a service server according to an embodiment of the present invention.

FIG. 5 is a block diagram schematically showing the configuration of a service server according to an embodiment of the present invention.

Referring to FIG. 5, the service server 200 includes a communication unit 210, a database 220, a walking path service unit 230, a recommendation unit 240 and a control unit 250.

The communication unit 210 may receive a walking path information request from a smart device through a communication network and transmit walking path information created by the walking path service unit 230 to the smart device 100. Here, the communication network includes both wired communication and wireless communication, and the smart device and the service server 200 are connected to each other through the communication networks.

Such a data communication unit 210 may include a variety of wired or wireless communication modules and transmit and receive data according to various wireless or wired communication specifications. For example, the data communication unit 210 can be implemented in a form including various standard communication modules of ITU, IEEE, ISO, IEC and the like or in a form including a variety of communication modules other than the standard communication modules.

The database 220 includes a map database and a user database.

Map information including map image information, scale information, coordinate information and the like is stored in the map database. In addition, indoor moving paths which move from a road to a road are stored in the map database. In addition, walking information including information on a building, indoor moving paths penetrating the inside of a facility, locations of entrances and exits, time for using the entrances and exits and the like are stored in the map database.

User information (a name, an address and the like), biometric information, location information and the like are stored in the user database.

These databases 220 can be implemented to meet the objects of the present invention using a relational database management system (RDBMS) such as Oracle, Infomix, Sybase, DB2 or the like or an object-oriented database management system (OODBMS) such as Gemston, Orion, O2 or the like and may include appropriate fields to accomplish their functions.

Although it is shown in the figure that the database 220 is included in the service server 200, the database 220 and the service server 200 may be separately configured according to the needs of those skilled in the art implementing the present invention.

If a walking path information request signal is received through the communication unit 210, the walking path service unit 230 creates a walking path from the starting point to the destination, calculates a time of arrival at the destination by the average walking speed of the created walking path, and transmits walking path information including the walking path and the time of arrival at the destination to the smart device. That is, if a walking path information request signal including the smart device identification information, the average walking speed, the starting point, the destination and the like is received, the walking path service unit 230 creates a walking path from the starting point to the destination using the map information stored in the map database. At this point, the walking path service unit 230 may create a shortest walking path.

That is, the walking path service unit 230 receives a starting point and a destination and creates a walking path, and if there is a reduced path passing through the inside of a building among the paths created between the starting point and the destination, the walking path service unit 230 may create the corresponding reduced path as a walking path. At this point, the walking path service unit 230 may search for coordinate information of the starting point and the destination, map image information of corresponding coordinates and scale information from map information stored in the map information database and create a walking path mainly focused on roads. That is, the walking path service unit 230 creates path information mainly focused on roads according to the starting point and the destination and determines whether or not a building storing an indoor moving path is included in the created path. If there is an indoor moving path as a result of the determination, the walking path service unit 230 creates path information including the indoor moving path. Like this, the walking path service unit 230 creates at least one or more pieces of path information including the walking path mainly focused on roads and the indoor moving path. In addition, the walking path service unit 230 creates an optimum walking path considering the number of waiting sections in the walking path and the moving distance between the starting point and the destination. The walking path service unit 230 may grasp at least one or more walking paths between the starting point and the destination and create, among the grasped walking paths, a walking path consuming the shortest time as an optimum walking path based on the moving distance and the number of waiting sections including crosswalks.

Then, the walking path service unit 230 calculates a time of arrival at the destination by the average walking speed of the walking path and transmits walking path information including the walking path and the time of arrival at the destination to the smart device.

If the moving speed is received from the smart device, the recommendation unit 240 determines whether or not the moving speed is lower than a preset threshold speed and recommends a taxi call service if the moving speed is lower than a preset threshold speed as a result of the determination. If the user desires to use the taxi call service, the recommendation unit 240 may search for an unoccupied taxi in the nearest distance from the current position of the user and provide taxi reservation information including the license plate number, an estimated arrival time and the like of the searched unoccupied taxi.

Meanwhile, the walking path service unit 230 and the recommendation unit 240 can be implemented by a processor or the like needed to execute a program on a computing device. Like this, each of the walking path service unit 230 and the recommendation unit 240 can be implemented by a physically independent configuration or implemented as a functionally separate form in a processor.

The control unit 250 is a configuration for controlling operation of various constitutional components of the service provider device (→ service server) 200 including the communication unit 210, the database 220, the walking path service unit 230 and the recommendation unit 240.

The control unit 250 may include at least one arithmetic unit, and, here, the arithmetic unit may be a general-purpose central processing unit (CPU), a programmable device element (CPLD or FPGA) implemented to be suitable for a specific purpose, an application specific integrated circuit (ASIC) or a microcontroller chip.

Figure 6:
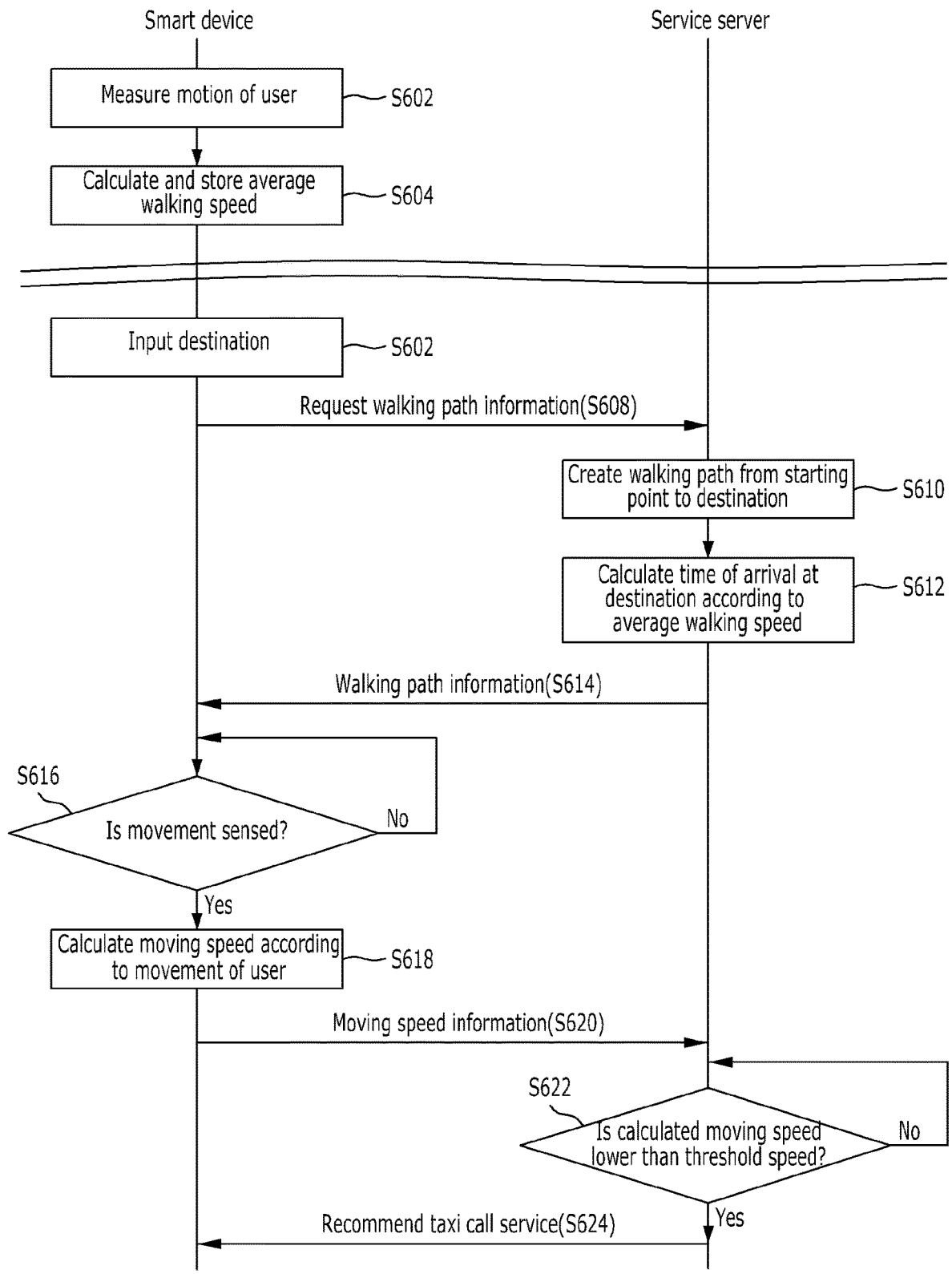
FIG. 6 is a sequence chart showing a method of providing a walking path guidance service based on measurement of a motion according to the present invention.

FIG. 6 is a sequence chart showing a method of providing a walking path guidance service based on measurement of a motion according to the present invention.

Referring to FIG. 6, the smart device measures a motion of a user (step S602) and calculates an average walking speed of the user using the measured motion (step S604). That is, the smart device detects steps using a motion measurement value of the sensor unit, calculates a moving distance of the user using the position information measured by the sensor unit, and analyzes an average number of steps according to the moving distance as a walking pattern. Then, the smart device obtains an average walking speed by dividing the moving distance by the moving time (average walking speed=moving distance/moving time). If a destination is input, the smart device transmits a walking path information request signal including the average walking speed and the destination to the service server.

Thereafter, if a destination is input (step S606), the smart device transmits a walking path information request signal including the smart device identification information, the average walking speed, the starting point, the destination and the like to the service server (step S608).

The service server creates a walking path from the starting point to the destination (step S610), calculates a time of arrival at the destination of the walking path according to the average walking speed (step S612) and transmits walking path information including the calculated time of arrival at the destination to the smart device (step S614). At this point, the service server may transmit the walking path together with the time of arrival at the destination.

The service server receives a starting point and a destination and creates a walking path, and if there is a reduced path passing through the inside of a building among the paths created between the starting point and the destination, the service server may create the corresponding reduced path as a walking path. In addition, the service server may create an optimum walking path considering the number of waiting sections in the walking path and the moving distance between the starting point and the destination.

Then, the service server may calculate a time of arrival at the destination using the distance and the average walking speed of the walking path and transmit the calculated time of arrival at the destination to the smart device.

If movement of the user according to the walking path is sensed (step S616), the smart device calculates a moving speed by measuring a motion of the user according to the movement (step S618) and transmits the calculated moving speed to the service server (step S620).

The service server determines whether or not the moving speed transmitted from the smart device is lower than a preset threshold speed (step S622) and recommends a taxi call service if the moving speed is lower than a preset threshold speed (step S624). If the user desires to use the taxi call service, the service server may search for an unoccupied taxi in the nearest distance from the current position measured by the sensor unit, transmit taxi reservation information including the license plate number, an estimated arrival time and the like of the searched unoccupied taxi to the smart device of the user, and transmit the user's position, user identification information (the phone number, the identification information of the smart device and the like) and the like to the driver of the searched taxi.

Since the present invention provides a system and method for providing a walking path guidance service based on measurement of a motion of a user, an estimated time of arrival at a destination according to an average walking speed of the user can be confirmed, and the user may arrive at the destination within the estimated time on foot.

In addition, since a taxi call service is recommended if the moving speed of the user is lower than a predetermined speed or too slow, the user may arrive at the destination within an estimated time.

In addition, if the moving speed of the user is lower than a predetermined speed or too slow, the reasons of delaying the walking can be understood and the health state of the user can be determined by measuring biometric information of the user.

Figure 7:
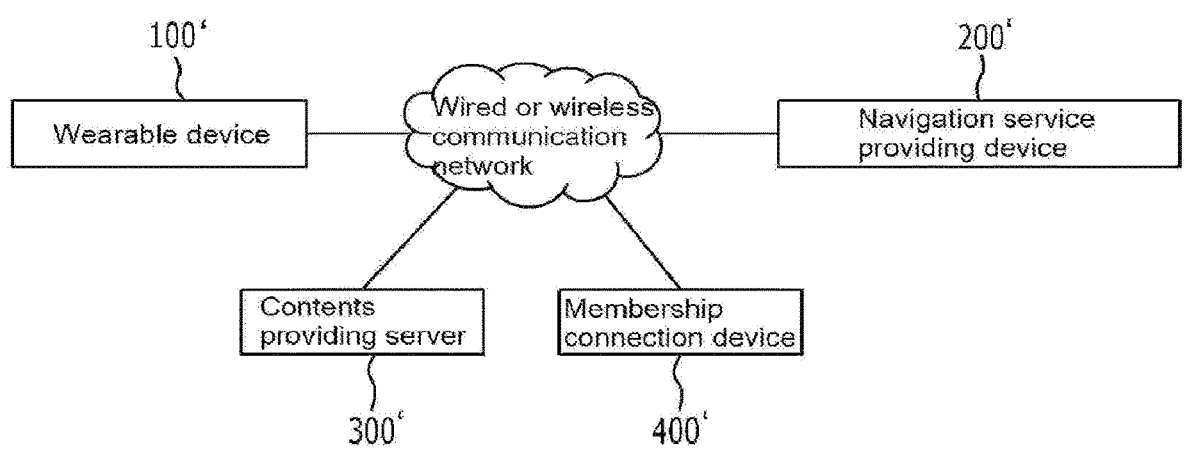
FIG. 7 is a view schematically showing a system for providing a navigation service using a wearable device according to an embodiment of the present invention.

FIG. 7 is a view schematically showing a system for providing a navigation service using a wearable device 100' according to an embodiment of the present invention.

At this point, the wearable device 100', a navigation service providing device 200', a contents providing server 300' and a membership connection device 400' are connected through a wired or wireless communication network, and, at this point, the communication network includes a base station controller, a base station transmitter and/or a relay. Here, the base station controller performs a function of relaying signals between the base station transmitter and a switching center. The communication network supports both synchronous and asynchronous types. Accordingly, in the case of the synchronous type, the transmitter of a transmission and reception base station will be a Base Station Transmission System (BTS), and the controller of the transmission and reception base station will be a Base Station Controller (BSC), whereas in the case of the asynchronous type, the transmitter of a transmission and reception base station will be a Radio Transceiver Subsystem (RTS), and the controller of the transmission and reception base station will be a Radio Network Controller (RNC). It is apparent that the communication network according to an embodiment of the present invention is not limited thereto, and it generally refers to a GSM network, not a CDMA network, and any one that can be used in an access network of a next-generation mobile communication system which will be implemented in the future.

The communication network may further include access points. The access point is a small base station such as a femto or pico base station frequently installed inside a building. Here, the femto or pico base station is categorized by the maximum number of servers and devices based on the classification of small base stations. In addition, the access point includes a short-range communication module for performing short-range communication with a portable terminal, such as Wi-Fi communication or the like. The short-range communication can be performed based on various specifications of Bluetooth communication, Zigbee communication, infrared communication (IrDA), Radio Frequency (RF) communication including Ultra High Frequency (UHF) and Very High Frequency (VHF), Ultra Wide Band (UWB) communication and the like, in addition to the Wi-Fi communication. The access point may extract a position of a data packet, assign a best communication path for the extracted position, and transfer the data packet to a next device, e.g., a wearable device 100', along the assigned communication path. The access point may share several circuits in a general network environment.

The access point is largely classified into a fixed access point and a mobile access point. The fixed access point may include a router, a repeater, a relay and the like, and the mobile access point may include a bridge product of a specific manufacturer such as Egg of KT Corporation. Such a mobile access point may read a receiving side address from the transmitting side information and transmit data after assigning a most suitable communication path while guaranteeing free mobility.

In the present invention, each device or server has a transmission and reception unit, and here, the transmission and reception unit includes an RF transmission means for up-converting the frequency of a transmitted signal and amplifying the signal and an RF reception means for low-noise amplifying a received signal and down-converting the frequency of the received signal. The transmission and reception unit may include at least one of a wireless communication module (not shown) and a wired communication module (not shown). In addition, the wireless communication module may include at least one of a wireless network communication module, a Wireless Local Area Network, Wireless Fidelity or Worldwide Interoperability for Microwave Access (WLAN, Wi-Fi or WiMAX) communication module and a Wireless Personal Area Network (WPAN) communication module.

The wireless communication module is a configuration for transmitting and receiving data according to a wireless communication method, and when a device or a server uses wireless communication, it may transmit or receive data for providing payment information using any one of the wireless network communication module, the wireless LAN communication module and the wireless PAN communication module.

Figure 8:
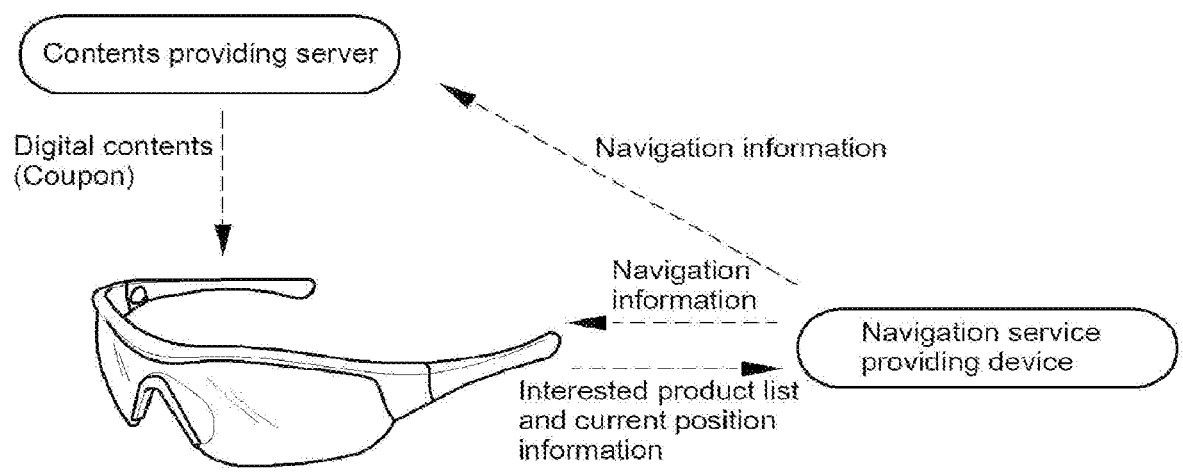
FIG. 8 is a view showing an example of providing a navigation service using a wearable device according to an embodiment of the present invention.

FIG. 8 is a view showing an example of providing a navigation service using a wearable device 100' according to an embodiment of the present invention.

A system for providing a navigation service using a wearable device 100' of the present invention includes the wearable device 100', a navigation service providing device 200' and a contents providing server 300'.

More specifically, the navigation service providing system includes a wearable device 100' for storing a list of interested products to be purchased, confirming whether a user has entered a store or arrived at a payment location by transmitting and receiving signals to and from a communication device installed in the store, and receiving navigation information data from the navigation service providing device 200' and displaying navigation information on the screen if entrance of the user into the store is confirmed; a navigation service providing device 200' for receiving the list of interested products from the wearable device 100', storing information on in-store products, creating navigation information using the stored information on in-store products and transferring the navigation information to the wearable device 100' or a contents providing server 300'; and the contents providing server 300' for transferring digital contents of interested products recorded in the navigation information received from the navigation service providing device 200' to the wearable device 100'.

At this point, of the term 'digital contents', the 'digital' means a method of expressing information, and the 'contents' generally refers to information, knowledge and database configured in a variety of forms such as a symbol, a character, a sound, a video, a picture, an image and the like, and although the digital contents are contents configured in the form of a character, a sound, a picture, a video and the like distributed using the Internet, they do not mean only information and simple contents, but mean contents of a form containing a transaction and a service as a property for creating an added value using various information techniques. For example, the digital contents include applications related to a service provided by a service provider, which can be transferred to the wearable device 100' or a smart terminal device and executed therein, electronic coupons related to a store, electronic coupons related to membership and the like.

In another embodiment of the present invention, the system for providing a navigation service using a wearable device 100' may further include a membership connection device 400'. At this point, the membership connection device 400' may perform authentication according to authentication information transferred from the contents providing server 300', transfer membership information of a user to the contents providing server 300' if it is confirmed that the user is a membership holder as a result of the authentication, and transmit a membership acquisition request message to the contents providing server 300' and the wearable device 100' if it is confirmed that the user is not a membership holder.

If the navigation service providing system includes the membership connection device 400', there is an effect of persuading a user to acquire a membership related to an affiliated company which provides digital contents and a service provider which provides a navigation service platform.

Meanwhile, such a membership connection device 400' is an additional component, and a digital contents providing service added to the navigation service can be directly provided to a user without authenticating the membership acquired through the membership connection device 400'.

Figure 9:
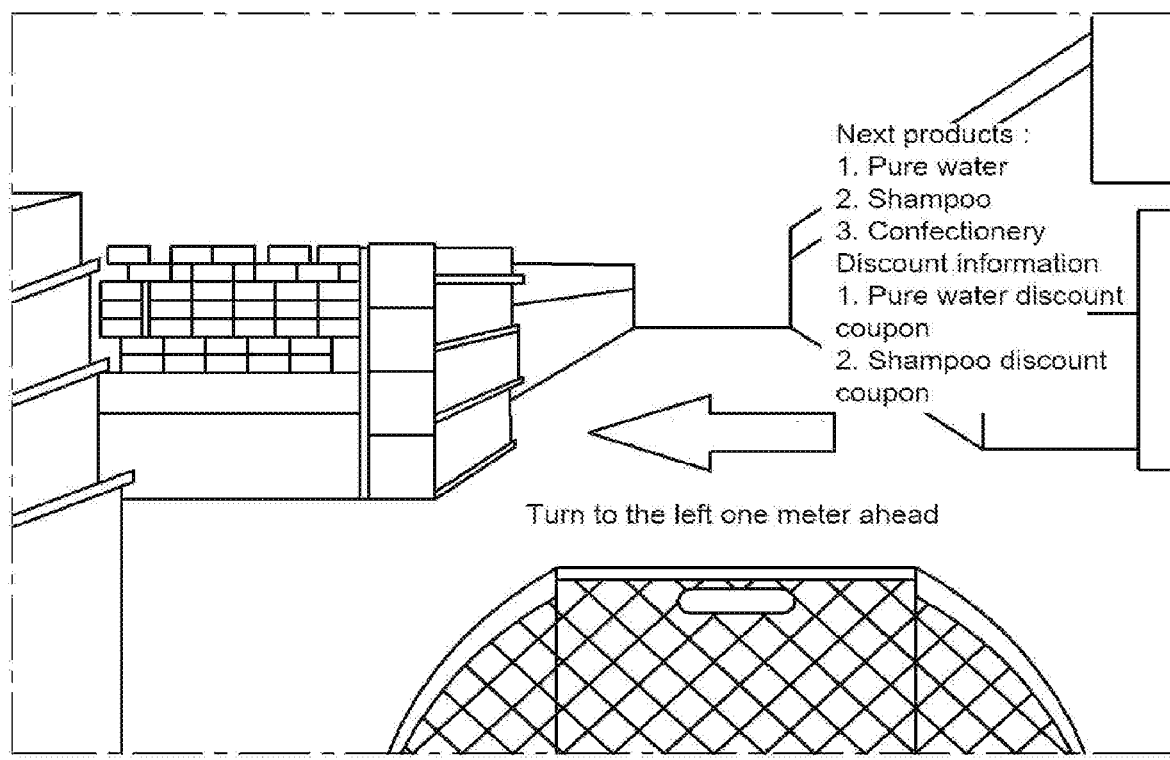
FIG. 9 is a view showing an example of providing a navigation service by a wearable device according to an embodiment of the present invention.

FIG. 9 is a view showing an example of providing a navigation service by a wearable device 100' according to an embodiment of the present invention.

Referring to FIG. 9, navigation information is provided while showing the products displayed in a store through a display screen of a wearable device 100', e.g., a smart glass, and at the same time, product information and discount information can be provided. Alternatively, the same information can be provided through a wearable device having a display screen, such as a smart band.

Figure 10:
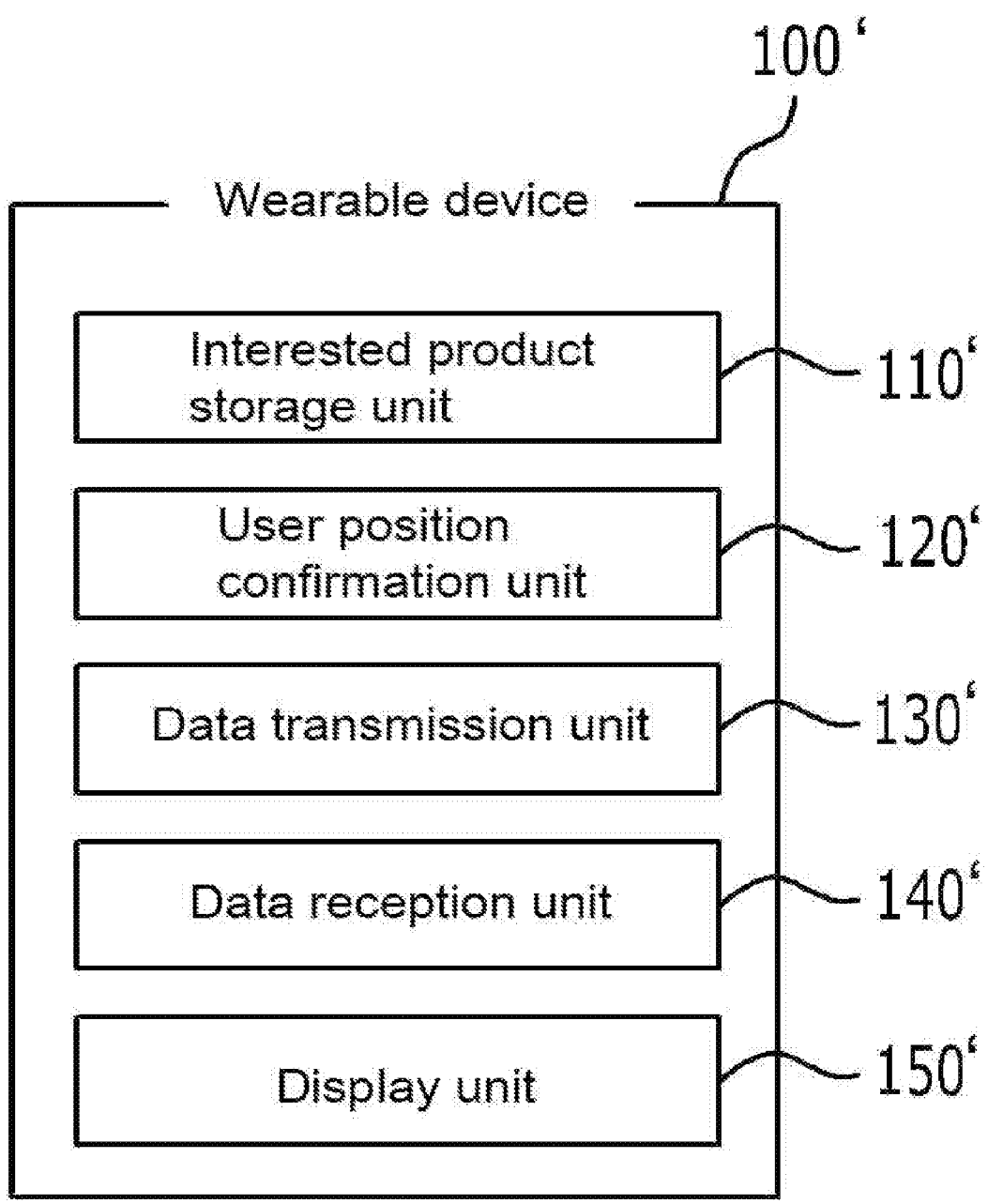
FIG. 10 is a block diagram showing the configuration of a wearable device according to an embodiment of the present invention.

FIG. 10 is a block diagram showing the configuration of a wearable device according to an embodiment of the present invention.

The wearable device 100' of the present invention includes an interested product storage unit 110', a user position confirmation unit 120', a data transmission unit 130', a data reception unit 140' and a display unit 150'. More specifically, the wearable device 100' includes an interested product storage unit 110' for storing a list of interested products to be purchased; a user position confirmation unit 120' for confirming whether a user has entered a store or arrived at a payment location by transmitting and receiving signals to and from a communication device installed in the store; a data transmission unit 130' for transferring current position information of the user and data on the list of interested products stored in the interested product storage unit 110' to the navigation service providing device 200' if entrance of the user into the store is confirmed by the user position confirmation unit 120'; a data reception unit 140' for receiving navigation information data of an interested product from the navigation service providing device 200'; and a display unit 150' for displaying navigation information of the interested product received by the data reception unit 140'.

The interested product storage unit 110' stores a list of interested products to be purchased. On the other hand, the interested product storage unit 110' may receive and store information on interested products input from an application installed in another smart terminal paired with the wearable device 100'.

The user position confirmation unit 120' confirms whether a user has entered a store and/or arrived at a payment location by transmitting and receiving signals to and from a communication device installed in the store.

At this point, the communication device installed in the store may use Wi-Fi or a beacon. This is a smart terminal short-range communication technique for finding a position of a user within a range of a 50 to 70 m radius and making message transmission, mobile payment or the like possible. Since the short-range communication has an available distance longer than that of near field communication (NFC), it is suitable for O2O service which connects on-line and off-line spaces. If this technique is used, a guidance service, a mobile coupon and the like can be used at a specific location.

This technique is utilized diversely, for example, if a customer using the service enters a store, the customer may automatically confirm product information, customer evaluation and the like and also receive a discount coupon.

In addition, since the short-range communication operates at a low power, consumption of the smart phone battery is low, and it can trace a location in a room more precisely than a GPS, and since a position of a smart phone user can be correctly grasped, it can be utilized for collection of personal information.

If entrance of the user into the store is confirmed by the user position confirmation unit 120', the data transmission unit 130' transfers current position information of the user and data on the list of interested products stored in the interested product storage unit 110' to the navigation service providing device 200'.

The data reception unit 140' receives navigation information data of an interested product from the navigation service providing device 200'. At this point, if a store manager changes information on a product recorded in the interested product list stored in the interested product storage unit 110' using a store terminal, the data reception unit 140' may receive product information data updated and stored in a product information database 220' of the navigation service providing device 200'.

At this point, if it is confirmed by the user position confirmation unit 120' that the user has arrived at the payment location, the data reception unit 140' may further receive digital contents transferred from the contents providing server 300'.

Meanwhile, in relation to the time point of receiving the digital contents by the data reception unit 140', it can be set to receive the digital contents when the user arrives at the payment location, or it may be set to directly provide the digital contents while the user is shopping. Even in the case of providing digital contents when it is confirmed that the user has arrived at the payment location, information on the type of digital contents can be provided for the interested products while the user is shopping.

The display unit 150' displays navigation information of the interested product received by the data reception unit 140' on the screen. At this point, the display unit 150' displays information on a series of operation states and operation results created while performing a function of the wearable device 100'. In addition, the display unit 150' may display a menu of the wearable device 100' and user data or the like input by the user. Here, the display unit 150' may be configured of a Liquid Crystal Display (LCD), a Thin Film Transistor LCD (TFT-LCD), Organic Light Emitting Diodes (OLED), LEDs, Active Matrix Organic LEDs (AMOLEDs), a flexible display, a three-dimensional display or the like. At this point, the display unit 150' may be configured in the form of a touch screen, and when the display unit 150' is configured in the form of a touch screen like this, the display unit 150' may perform some or all of the functions of an input unit. Particularly, the display unit 150' according to an embodiment of the present invention displays navigation information received from the navigation service providing device 200' and digital contents transferred from the contents providing server 300'.

In addition, navigation information and digital contents provided to another smart terminal, e.g., a smart glass, paired with the wearable device 100' may be displayed on an application of a smart phone associated with the smart glass.

On the other hand, when the data reception unit 140' further receives the digital contents, the display unit 150' may simultaneously display the received digital contents on the screen.

Figure 11:
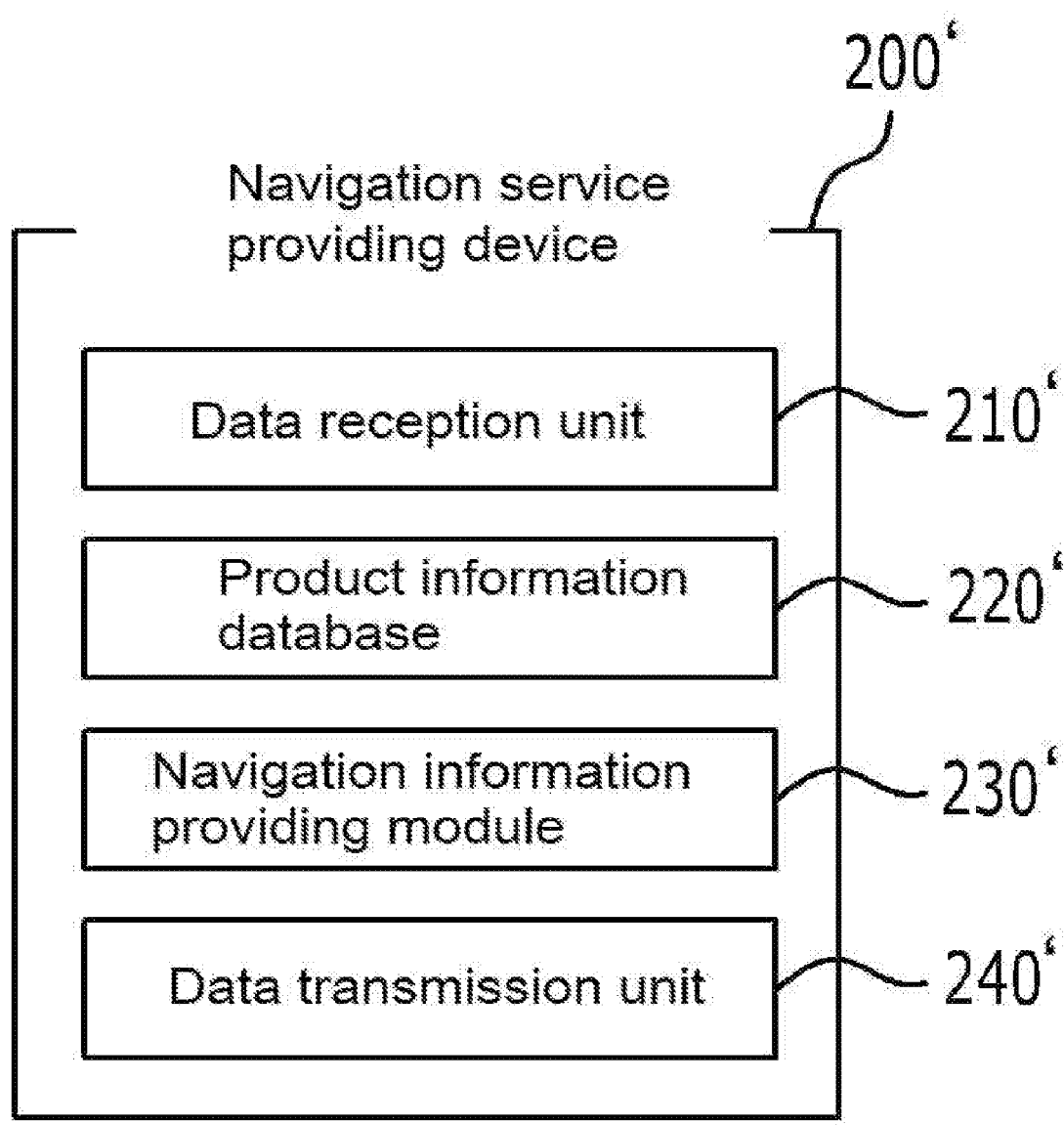
FIG. 11 is a block diagram showing the configuration of a navigation service providing device according to an embodiment of the present invention.

FIG. 11 is a block diagram showing the configuration of a navigation service providing device 200' according to an embodiment of the present invention.

The navigation service providing device 200' of the present invention includes a data reception unit 210', a product information database 220', a navigation information providing module 230' and a data transmission unit 240'.

More specifically, the navigation service providing device 200' includes a data reception unit 210' for receiving current position information of a user and an interested product list data from the wearable device 100'; a product information database 220' for storing information on in-store products; a navigation information providing module 230' for providing navigation information of the interested product list data received by the data reception unit 210' using the in-store product information stored in the product information database 220'; and a data transmission unit 240' for transferring the navigation information data provided by the navigation information providing module 230' to the wearable device 100'.

The data reception unit 210' receives current position information of a user, which is used as a starting point of a moving path or moving path information, and an interested product list data from the wearable device 100'.

The product information database 220' stores information on in-store products.

At this point, the product information database 220' may store product information updated by a store manager in real-time using a store terminal.

The navigation information providing module 230' provides navigation information of the interested product list data received by the data reception unit 210' using the in-store product information stored in the product information database 220'.

The data transmission unit 240' transfers the navigation information data provided by the navigation information providing module 230' to the wearable device 100'. At this point, the data transmission unit 240' may further transfer the navigation information data of the interested products provided by the navigation information providing module 230' to the contents providing server 300'.

Figure 12:
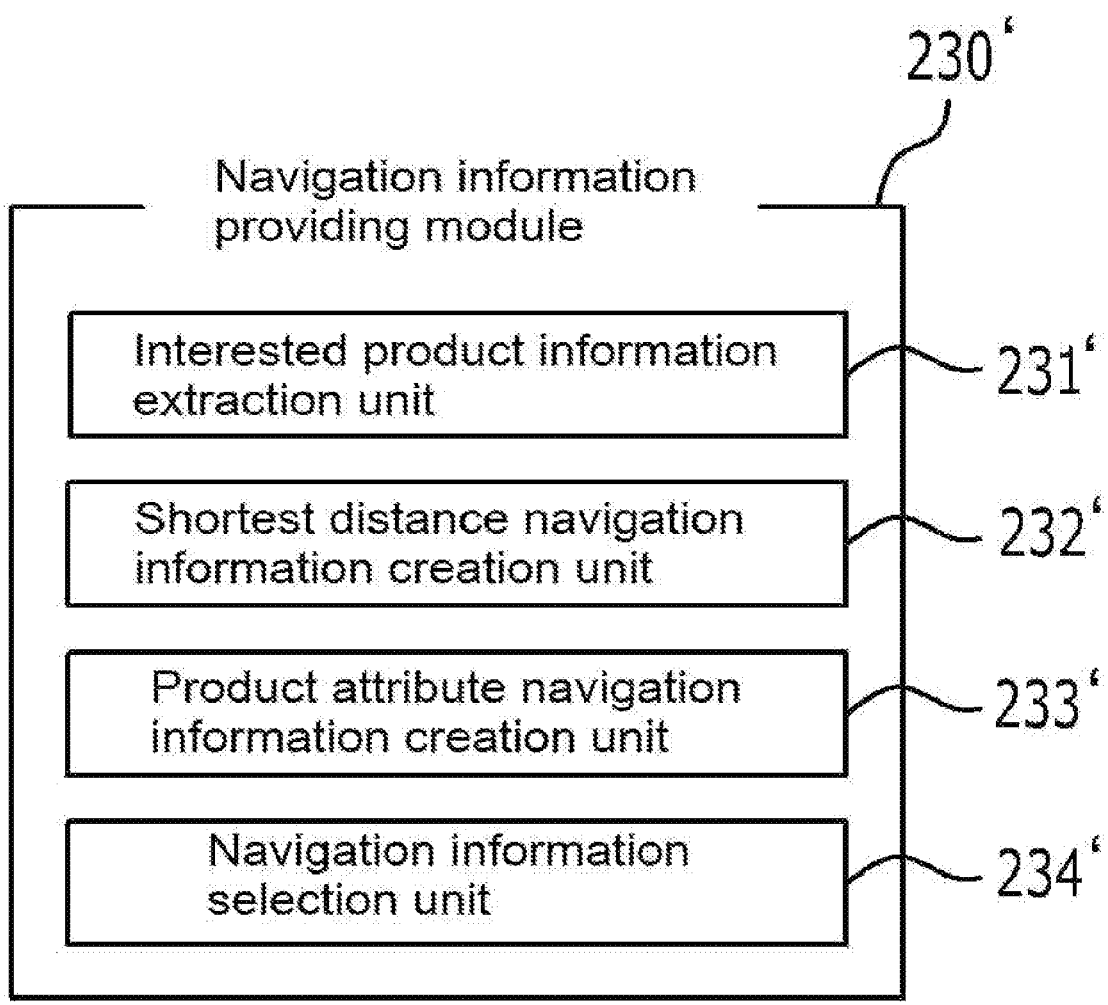
FIG. 12 is a block diagram showing the configuration of a navigation information providing module according to an embodiment of the present invention.

FIG. 12 is a block diagram showing the configuration of a navigation information providing module 230' according to an embodiment of the present invention.

The navigation information providing module 230' of the navigation service providing device 200' of the present invention includes an interested product information extraction unit 231', a shortest distance navigation information creation unit 232', a product attribute navigation information creation unit 233' and a navigation information selection unit 234'. More specifically, the navigation information providing module 230' includes an interested product information extraction unit 231' for extracting product information of interested products recorded in the interested product list from the database; a shortest distance navigation information creation unit 232' for creating shortest distance information by analyzing positions of at least one or more interested products using position information among the information on the interested products extracted by the interested product information extraction unit 231'; a product attribute navigation information creation unit 233' for creating navigation information using product attribute information among the information on the interested products extracted by the interested product information extraction unit 231'; and a navigation information selection unit 234' for selecting and providing navigation information according to a preset priority.

The interested product information extraction unit 231' extracts product information of interested products recorded in the interested product list from the database.

The shortest distance navigation information creation unit 232' creates shortest distance information by analyzing positions of at least one or more interested products using position information among the information on the interested products extracted by the interested product information extraction unit 231'.

The product attribute navigation information creation unit 233' creates navigation information using product attribute information among the information on the interested products extracted by the interested product information extraction unit 231'. At this point, the product attribute information may include any one or more pieces of information among the category, quantity and weight of the product, and various product attribute information may be included in addition to the product attribute information described herein.

The navigation information selection unit 234' selects and provides navigation information according to a preset priority. The priority described here means that which navigation information will be preferentially provided among the created navigation information, which refers to navigation information preferentially selected by the setting of the user or a service provider.

At this point, the navigation information can be selected in various ways. That is, the navigation information selection unit 234' may select navigation information by simultaneously considering the shortest distance information created by the shortest distance navigation information creation unit 232' and the product attribute navigation information created by the product attribute navigation information creation unit 233', and as an example of utilizing the two types of navigation information created as described above, if the shortest distance for purchasing a product according to the shortest distance navigation information is within a preset distance (e.g., 0.1 km), navigation information can be selected according to the product attribute navigation information created by the product attribute navigation information creation unit 233'. It is since that, generally, it is advantageous to use the short distance information as is if there are a lot of things to purchase and thus the entire shopping distance is long, and it is advantageous to use the navigation information according to the product attribute to put a heavy product in the lowest compartment of a cart if the shopping distance short. For example, referring to FIG. 9, the user is guided to the places where products are displayed in order of 1. Pure water, 2. Shampoo and 3. Confectionery, and this is a case of using weight information among the product attribute information.

On the other hand, the navigation information selection unit 234' may select any one of the shortest distance information created by the shortest distance navigation information creation unit 232' and the product attribute navigation information created by the product attribute navigation information creation unit 233'.

At this point, if the navigation information selection unit 234' selects the shortest distance information created by the shortest distance navigation information creation unit 232', a moving path for dropping in at least one or more interested products from the current position of the user terminal or shortest distance navigation information for moving from an interested product visited last to a payment location can be provided. For example, when the user needs to shop in a rush, this may help the user to shop by selecting the shortest distance navigation information as described above.

On the other hand, if the navigation information selection unit 234' selects the product attribute navigation information created by the product attribute navigation information creation unit 233', navigation information can be provided according to preset product attribute information.

For example, when the user desires to purchase products that can be easily spoilt as time goes by, such as sea food or ice cream, among the products to be purchased, the product attribute navigation information can be selected as described above.

Figure 13:
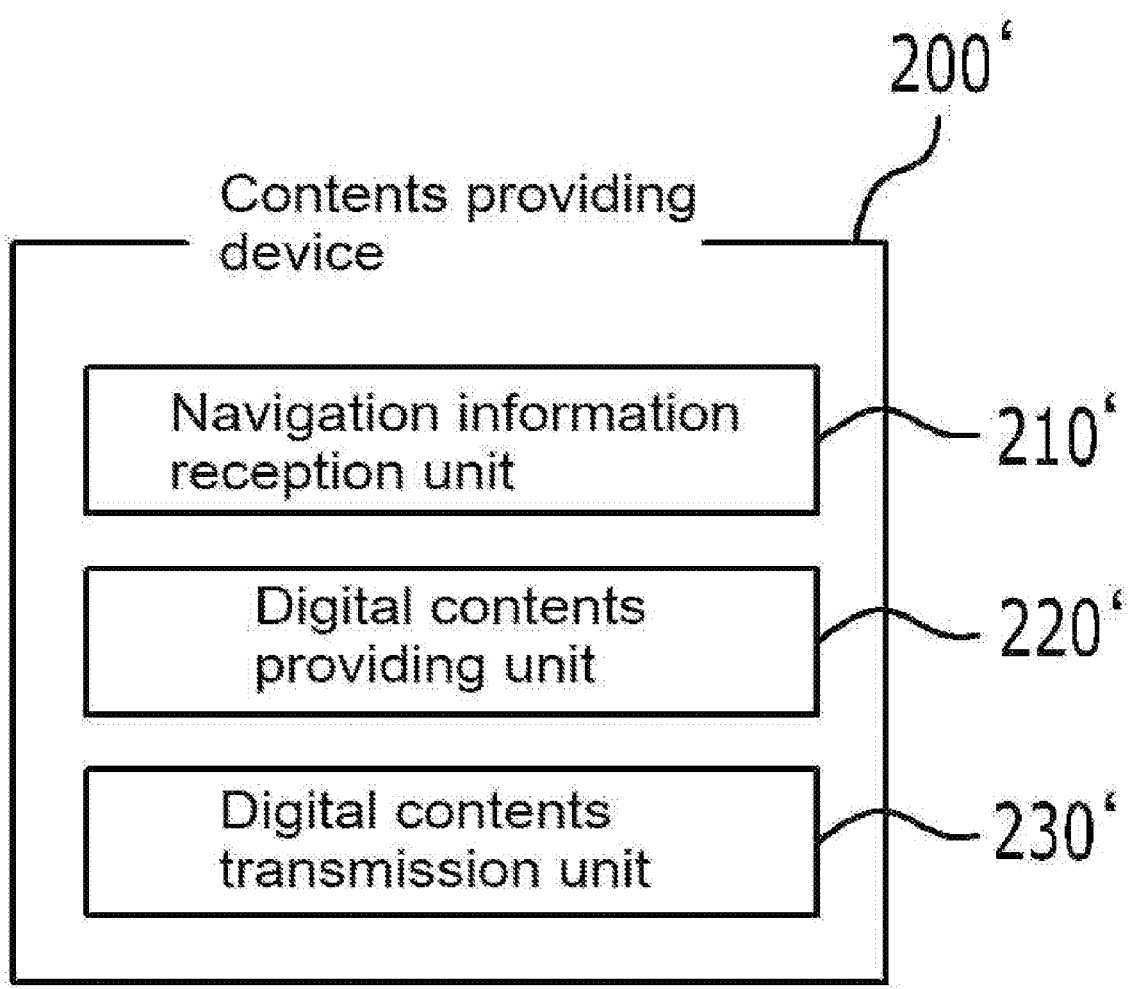
FIG. 13 is a block diagram showing the configuration of a contents providing server according to an embodiment of the present invention.

FIG. 13 is a block diagram showing the configuration of a contents providing server 300' according to an embodiment of the present invention.

The contents providing server 300' according to an embodiment of the present invention includes a navigation information reception unit 310', a digital contents providing unit 320' and a digital contents transmission unit 330'.

More specifically, the contents providing server 300' includes a navigation information reception unit 310' for receiving navigation information from the navigation service providing device 200'; a digital contents providing unit 320' for transferring digital contents of an interested product recorded in the navigation information received by the navigation information reception unit 310' to the digital contents transmission unit 330'; and a digital contents transmission unit 330' for transferring the digital contents transferred by the digital contents providing unit 320' to the wearable device 100'.

The navigation information reception unit 310' receives navigation information for providing appropriate digital contents to a service user from the navigation service providing device 200'. The received navigation information means navigation information containing information on the latest interested products transmitted from the service user in real-time.

The digital contents providing unit 320' transfers digital contents of an interested product recorded in the navigation information received by the navigation information reception unit 310' to the digital contents transmission unit 330'. The digital contents providing unit 320' may transfer a list of coupons that can be provided by a digital contents server to the digital contents transmission unit 330' based on the information.

The digital contents transmission unit 330' transfers the digital contents transferred by the digital contents providing unit 320' to the wearable device 100'.

On the other hand, the contents providing server 300' may further include an authentication information transmission unit for transferring authentication information to the membership connection device 400' to confirm whether or not a user holds membership of an affiliated company or a navigation service provider related to the digital contents transferred by the digital contents providing unit 320' to the wearable device 100'.

At this point, the phone number and the name of the user, details of the provided contents and other diverse information can be used as the authentication information.

Figure 14:
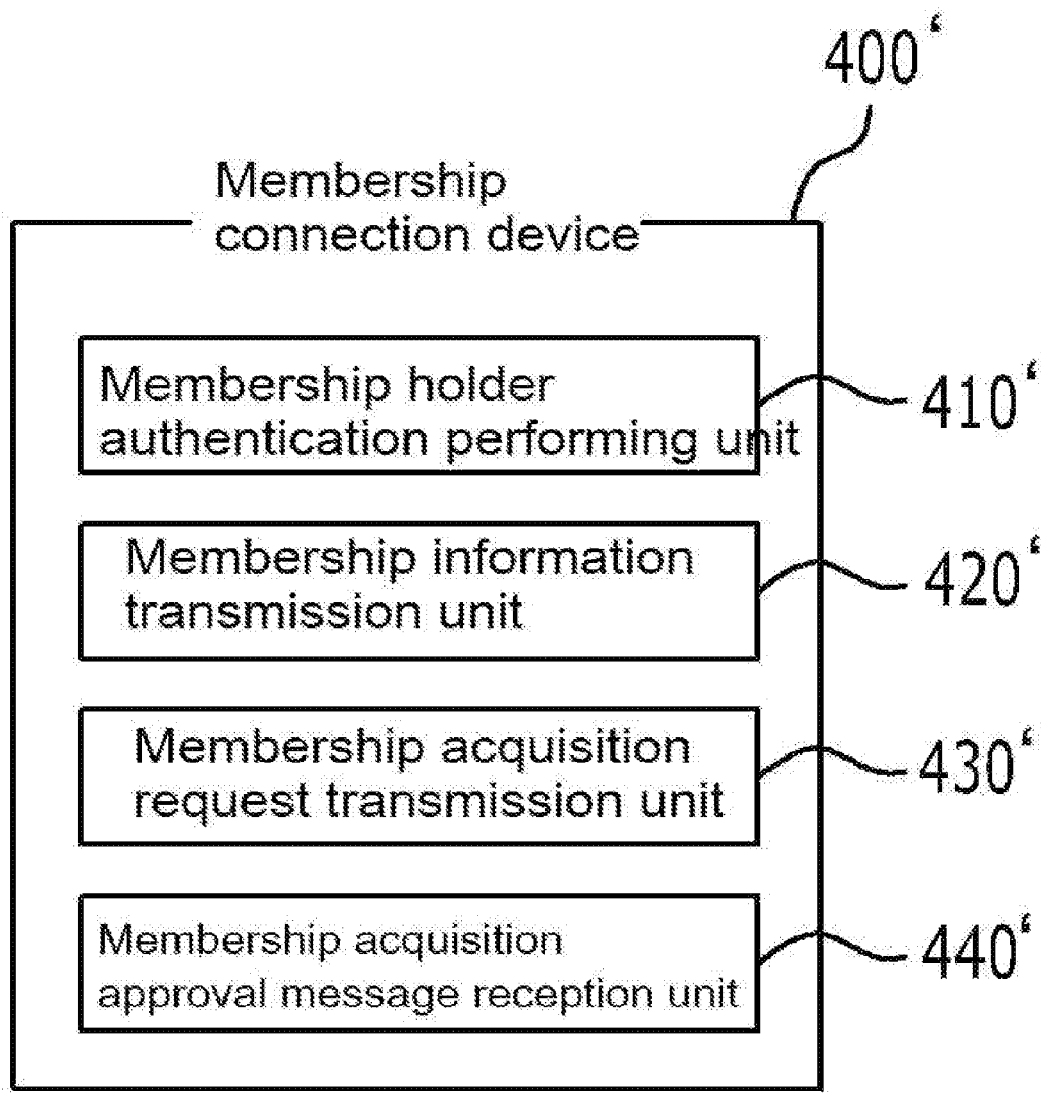
FIG. 14 is a block diagram showing the configuration of a membership connection device according to an embodiment of the present invention.

FIG. 14 is a block diagram showing the configuration of a membership connection device 400' according to an embodiment of the present invention.

The membership connection device 400' according to an embodiment of the present invention includes a membership holder authentication performing unit 410', a membership information transmission unit 420', a membership acquisition request transmission unit 430' and a membership acquisition approval message reception unit 440'.

More specifically, the membership connection device 400' includes a membership holder authentication performing unit 410' for performing authentication according to authentication information transferred from the contents providing server 300'; a membership information transmission unit 420' for transferring membership information of a user to the contents providing server 300' if it is confirmed that the user is a membership holder as a result of the authentication of the membership holder authentication performing unit; a membership acquisition request transmission unit 430' for transmitting a membership acquisition request message to the wearable device 100' if it is confirmed that the user is not a membership holder as a result of the authentication of the membership holder authentication performing unit; and a membership acquisition approval message reception unit 440' for receiving a membership acquisition approval message transmitted from the wearable device 100' in response to the membership acquisition request message.

The membership information transmission unit 420' transfers membership information of the user to the contents providing server 300' if it is confirmed that the user is a membership holder as a result of the authentication of the membership holder authentication performing unit. If the membership information transmission unit 420' transfers the membership information to the contents providing server 300', the contents providing server 300' may obtain a right for transferring digital contents (coupons) to the service user. Through the process like this, an effect of persuading a navigation service user to subscribe a service of an affiliated company which provides corresponding digital contents (coupons) is generated.

If it is confirmed that the user is not a membership holder as a result of the authentication of the membership holder authentication performing unit, the membership acquisition request transmission unit 430' transmits a membership acquisition request message to the wearable device 100'.

The membership acquisition approval message reception unit 440' receives a membership acquisition approval message transmitted from the wearable device 100' in response to the membership acquisition request message.

Meanwhile, in the present invention, the membership connection device 400' is a device (a server) for inducing acquisition of membership, which is a configuration that can be further included by the need of a navigation service provider or a platform provider.

Figure 15:
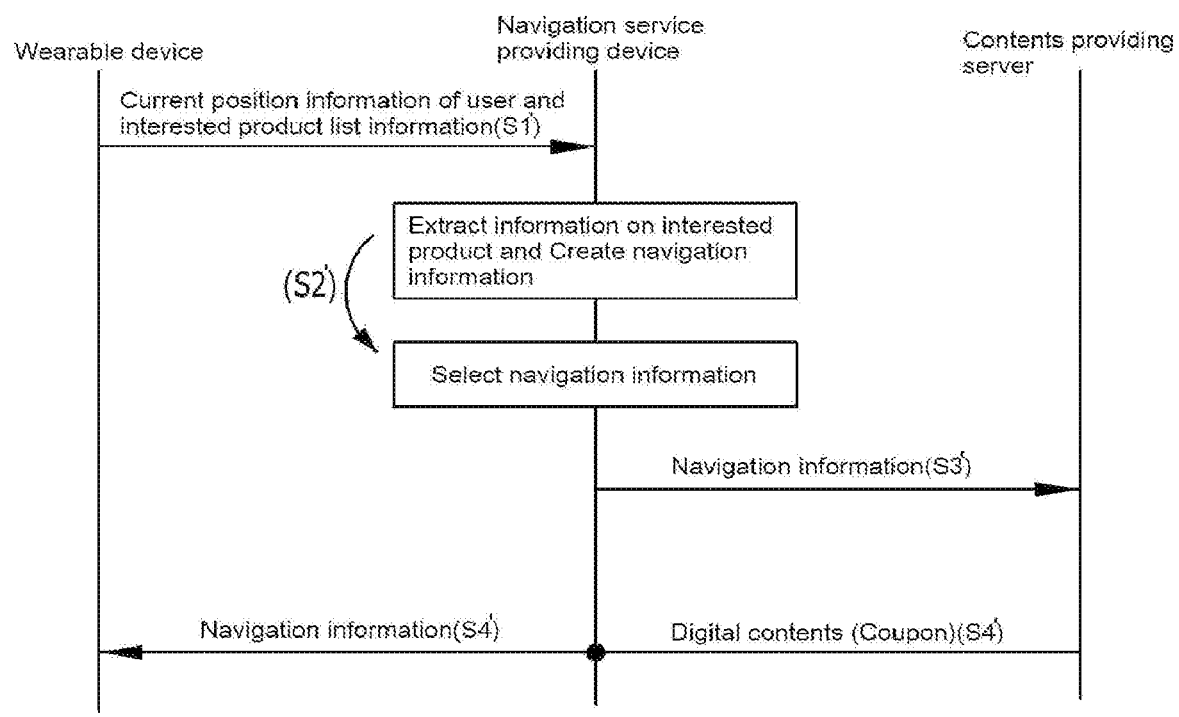
FIG. 15 is a sequence chart showing a navigation service providing method of a navigation service providing system according to an embodiment of the present invention.

FIG. 15 is a sequence chart showing a navigation service providing method of a navigation service providing system according to an embodiment of the present invention.

A method of providing a navigation service by the navigation service providing system according to an embodiment of the present invention includes the steps of (1) confirming whether a user enters a store by transmitting and receiving signals to and from a communication device installed in the store and transferring current position information of the user and an interested product list data to the navigation service providing device 200' if it is confirmed that the user enters the store, (step S1); (2) creating one or more pieces of navigation information and selecting navigation information after extracting information on an interested product using the current position information of the user and the interested product list data transferred in step (1), by the navigation service providing device (step S2); (3) transferring the navigation information selected at step (2) to the contents providing server, by the navigation service providing device (step S3); and (4) receiving the navigation information or the digital contents transferred at step (3), by the contents providing device 300' or the wearable device 100' (step S4).

Meanwhile, at step (4), the digital contents can be provided together with the navigation information or provided to a smart terminal or the wearable device 100' in a pop-up form if the user enters a payment location.

Figure 16:
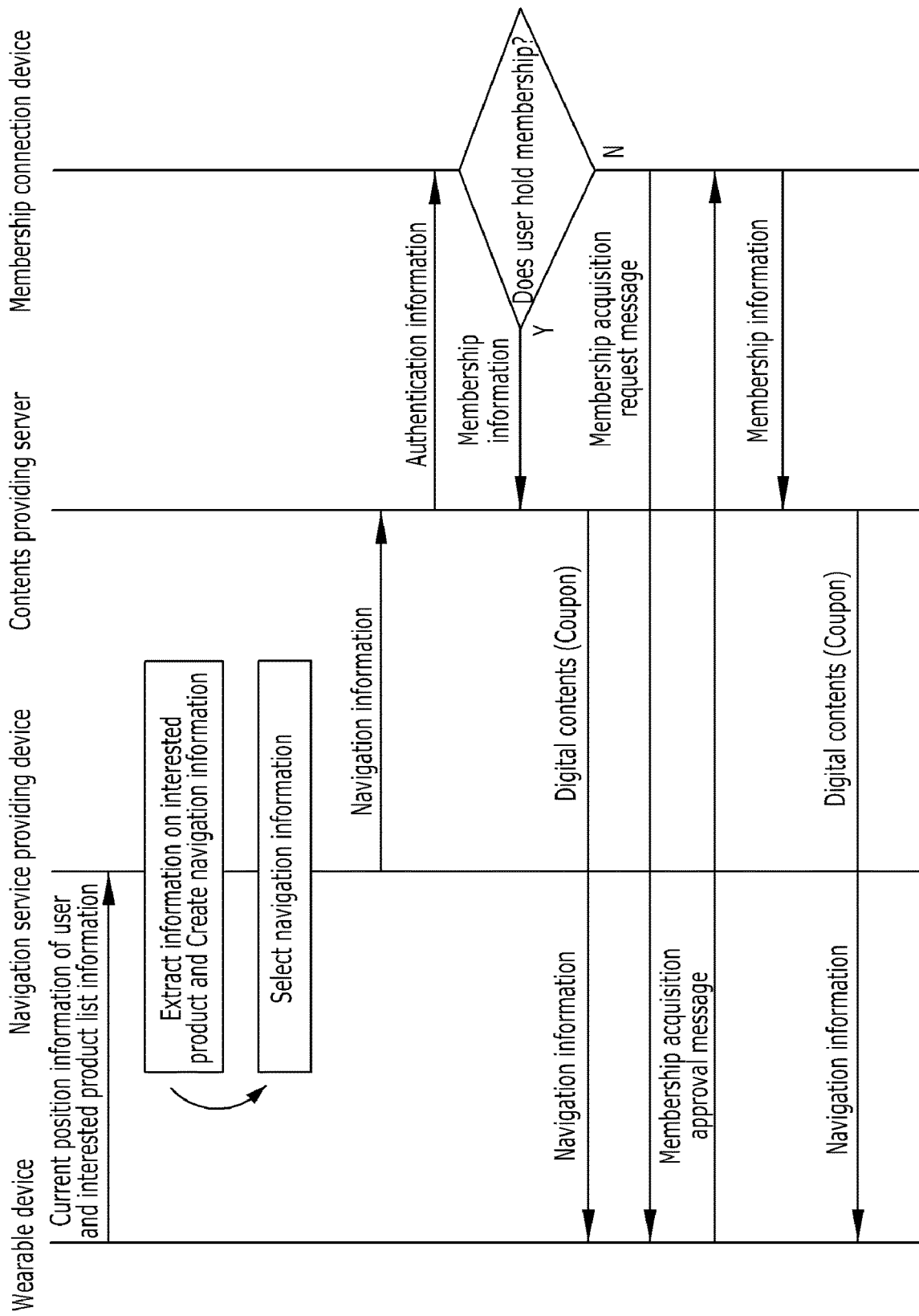
FIG. 16 is a sequence chart showing a method of providing a navigation service by performing authentication using a membership connection device according to another embodiment of the present invention.

On the other hand, referring to FIG. 16, the method of providing a navigation service may further include, after step (3) and before step (4), the steps of (a) confirming, by the membership connection device 400', whether or not a user holds membership of an affiliated company which provides digital contents using user authentication information transferred from the contents providing server 300'; (b) transferring, by the membership connection device 400', membership information of the user to the contents providing server 300' if it is confirmed that the user is a membership holder at step (a) and transferring a membership acquisition request message to the contents providing server 300' and the wearable device 100' if it is confirmed that the user is not a membership holder at step (a); and (c) Transferring the membership information of the user to the contents providing server 300' if a membership acquisition approval message is transferred from the wearable device 100' in response to the membership acquisition request message transferred at step (b).

A method of providing a navigation service by the contents providing server 300' according to an embodiment of the present invention includes (1) a navigation information receiving step of receiving navigation information from the navigation service providing device 200'; (2) a digital contents providing step of transferring digital contents of an interested product recorded in the navigation information received at step (1) to the digital contents transmission unit 330'; and (3) a digital contents transmitting step of transferring the digital contents transferred at step (2) to the wearable device 100'.

On the other hand, the method of providing a navigation service may further include, after step (2) and before step (3), an authentication information transmitting step of transferring authentication information to the membership connection device 400' to confirm whether or not a user holds membership of an affiliated company or a navigation service provider related to the digital contents.

A method of providing a navigation service by the membership connection device 400' according to an embodiment of the present invention includes (1) a membership holder authentication performing step of performing authentication according to authentication information transferred from the contents providing server 300'; (2) a step of transferring membership information of a user to the contents providing server 300' if it is confirmed that the user is a membership holder as a result of the authentication at step (1) and transmitting a membership acquisition request message to the wearable device 100' if it is confirmed that the user is not a membership holder; and (3) a membership acquisition approval message receiving step of receiving a membership acquisition approval message transmitted from the wearable device 100' in response to the membership acquisition request message transmitted at step (2).

As described above, according to the present invention, since navigation information of an interested product is provided using a wearable device 100', a user may visually confirm a moving path with ease and move to a place where the interested product is placed. In addition, since a service associated with digital contents is provided in real-time using the navigation information, benefits such as digital contents (coupons) or the like can be provided to a service user, and since an optimum moving path can be provided to the current navigation service user by utilizing attribute information of the products to be purchased, the user may conveniently enjoy shopping, and since a shortest moving path can be provided using locations of products to be purchased by the navigation service users, the user may promptly purchase the interested products.

Figure 17:
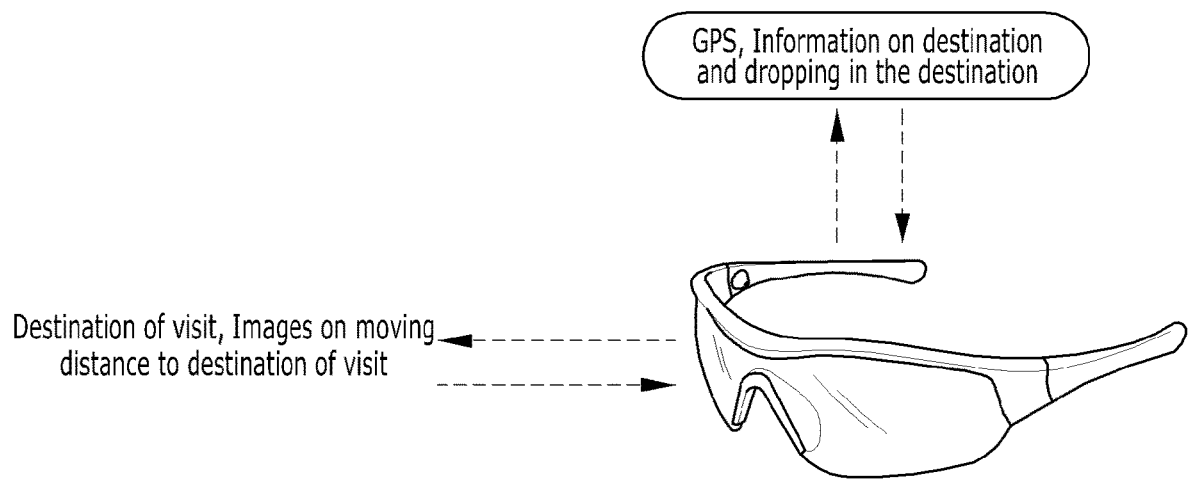
FIG. 17 is a view showing an example of collecting data, together with images related to visiting a store, by a wearable device according to an embodiment of the present invention.

FIG. 17 is a view showing an example of collecting data, together with images related to visiting a store, by a wearable device according to an embodiment of the present invention.

Figure 18:
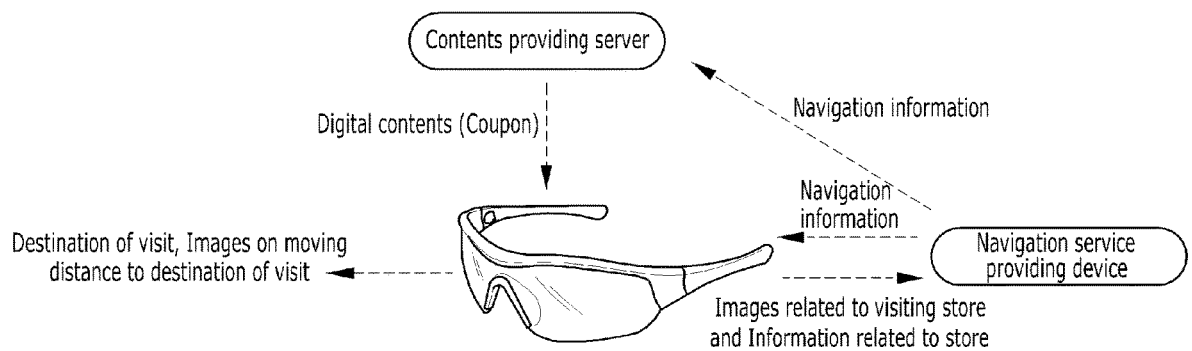
FIG. 18 is a view showing an example of providing a navigation service using a wearable device according to an embodiment of the present invention.

FIG. 18 is a view showing an example of providing a navigation service using a wearable device according to an embodiment of the present invention.

Figure 19:
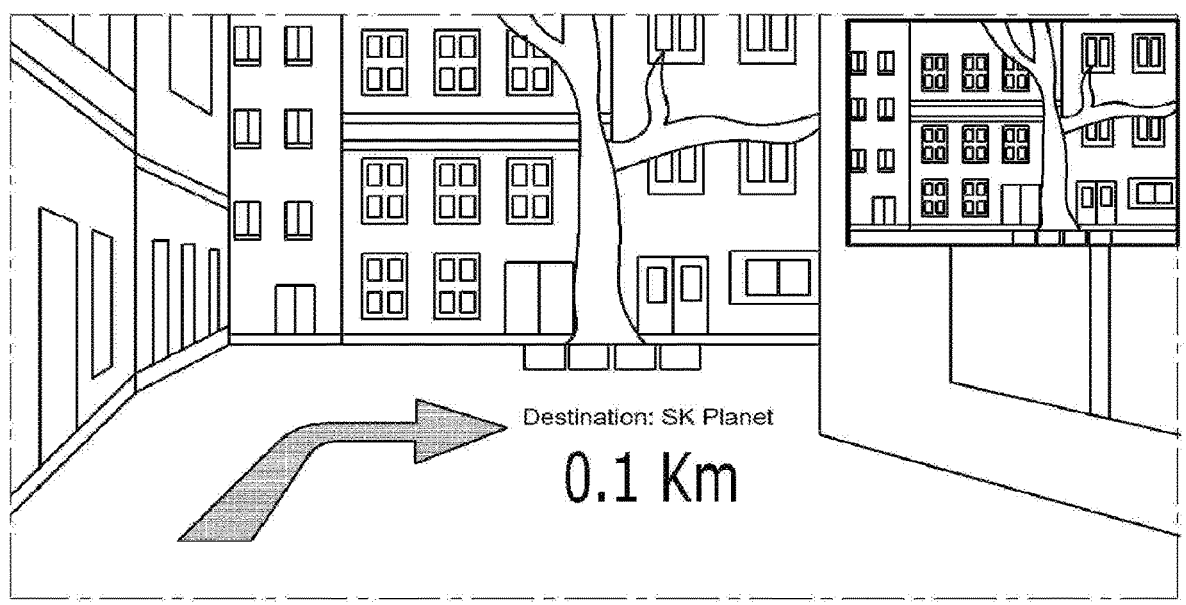
FIG. 19 is a view showing an example of providing a navigation service by a wearable device according to an embodiment of the present invention.

FIG. 19 is a view showing an example of providing a navigation service by a wearable device according to an embodiment of the present invention.

Referring to FIGS. 17 to 19, the navigation service providing system according to an embodiment of the present invention includes a wearable device, a navigation service providing device and a contents providing server. More specifically, the navigation service providing system includes a wearable device for photographing images related to visiting a store while moving to the store, which is the object of the visit, transferring the images photographed by a camera module in relation to visiting the store and information related to the store to the navigation service providing device, receiving digital contents transferred by the contents providing server and navigation information transferred by the navigation service providing device, and displaying the navigation information or the digital contents on a screen; the navigation service providing device for receiving and storing the images related to visiting a store and the information related to the store from one or more wearable devices of users, selecting navigation information using the images related to visiting a store and the information related to the store, and transferring the navigation information to the wearable devices and the contents providing server; and the contents providing server for receiving the navigation information from the navigation service providing device and transferring digital contents of a store recorded in the received navigation information as a point to drop in or visit to the wearable devices.

Here, of the term 'digital contents', the 'digital' means a method of expressing information, and the 'contents' generally refers to information, knowledge and database configured in a variety of forms such as a symbol, a character, a sound, a video, a picture, an image and the like, and although the digital contents are contents configured in the form of a character, a sound, a picture, a video and the like distributed using the Internet, they do not mean only information and simple contents, but mean contents of a form containing a transaction and a service as a property for creating an added value using various information techniques. For example, the digital contents include applications related to a service provided by a service provider, which can be transferred to the wearable device or a smart terminal device and executed therein, electronic coupons related to a store, electronic coupons related to membership and the like.

In another embodiment of the present invention, the system for providing a navigation service using a wearable device may further include a membership connection device. At this point, the membership connection device may perform authentication according to authentication information transferred from the contents providing server, transfer membership information of a user to the contents providing server if it is confirmed that the user is a membership holder as a result of the authentication, and transmit a membership acquisition request message to the contents providing server and the wearable device if it is confirmed that the user is not a membership holder.

If the navigation service providing system includes the membership connection device, there is an effect of persuading a user to acquire a membership related to an affiliated company which provides digital contents and a service provider which provides a navigation service platform.

Meanwhile, such a membership connection device is an additional component, and a digital contents providing service added to the navigation service can be directly provided to a user without authenticating membership acquired through the membership connection device.

Figure 20:
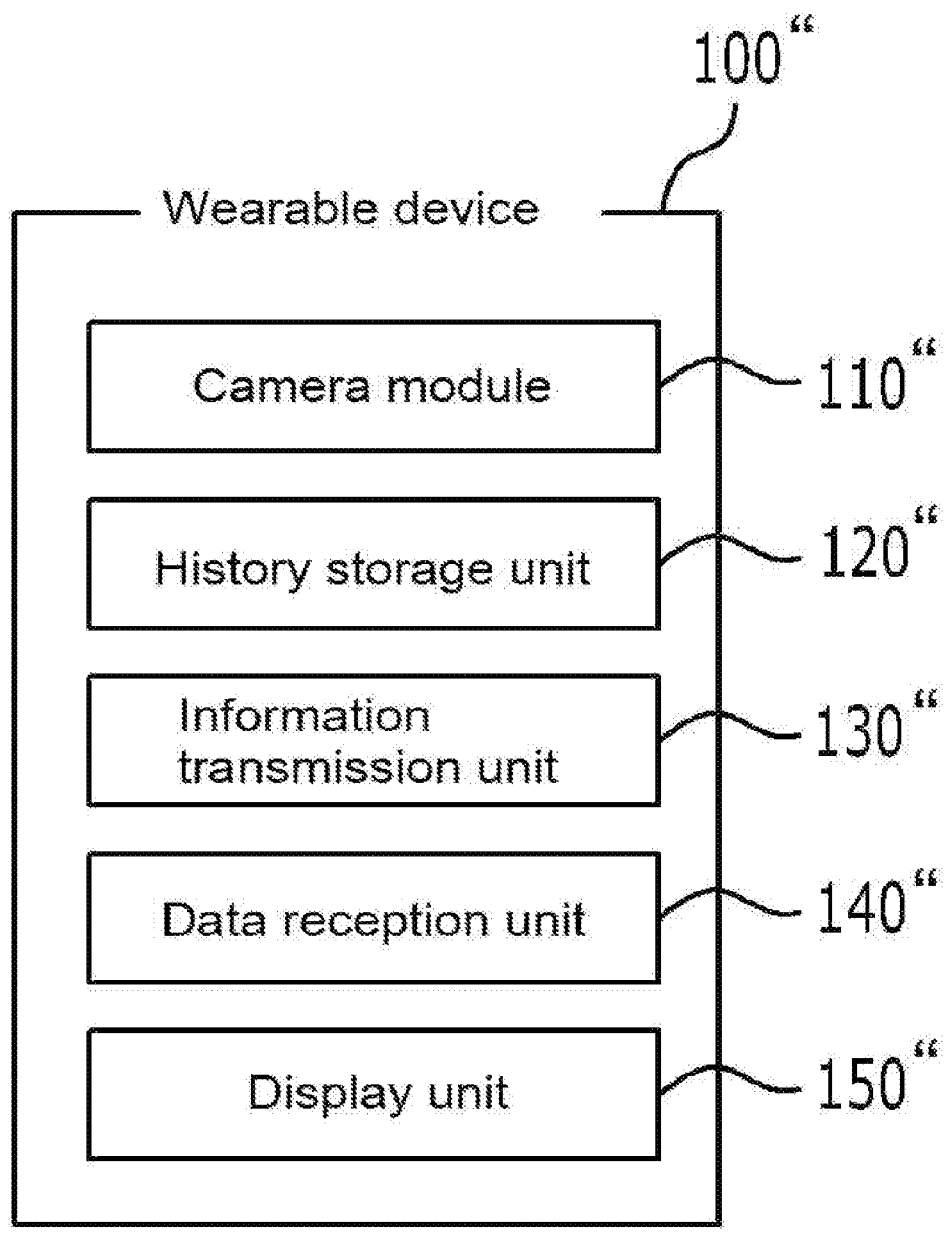
FIG. 20 is a block diagram showing the configuration of a wearable device according to an embodiment of the present invention.

FIG. 20 is a block diagram showing the configuration of a wearable device 100" according to an embodiment of the present invention.

The wearable device 100" according to an embodiment of the present invention includes a camera module 110", a history storage unit 120", an information transmission unit 130", a data reception unit 140" and a display unit 150".

More specifically, the wearable device 100" includes a camera module 110" for photographing images related to visiting a store while moving to the store, which is the object of the visit; a history storage unit 120" for storing the images photographed by the camera module 110" in relation to visiting the store and information related to the store; an information transmission unit 130" for transferring the images related to the store and the information related to the store, stored in the history storage unit 120", to the navigation service providing device 200"; a data reception unit 140" for receiving the navigation information transferred from the navigation service providing device 200"; and a display unit 150" for displaying the navigation information received by the data reception unit 140" on the screen.

The camera module 110" photographs images related to visiting a store while moving to the store, which is the object of the visit. This means a camera module 110" embedded in a wearable device 100", and preferably, a camera module 110" mounted on a smart glass can be used. When a camera module 110" mounted on a smart glass is used, it is advantageous in that since images at a point where the eyes stay can be photographed when the camera module 110" moves toward a destination following the eyeline of the user, images related to the destination can be photographed rapidly and correctly compared with a case of using a camera module 100" embedded in a general terminal device such as a smart phone. For example, when the user moves toward a specific destination, it is highly probable that the point where the eyes of the service user stay on the path moving to the destination is the front side and the eyes will stay at specific landmarks, and thus these can be rapidly and correctly photographed.

The history storage unit 120" stores the images photographed by the camera module 110" in relation to visiting the store and information related to the store. At this point, the images related to visiting a store means images of the places photographed every preset time or every preset distance by the camera module 110" while moving to the store, which is the object of the visit. The information related to a store stored in the history storage unit 120" means position information of a place where the camera module 110" photographs images related to visiting a store, path information used to move to the store from the place where the images related to the store are photographed by the camera module 110", information on other stores close to the visited store, and information on the visited store.

Meanwhile, information on the visited store may be information on the location of the store, information on the business type of the store and information on details of using the digital contents at the store.

Meanwhile, it may be set to acquire images every specific time or every specific distance by the service user or the service platform provider. For example, if the moving speed is low, it may be set to acquire an image every two minutes, and if the moving speed is high, it may be set to acquire an image every one minute, and in the case of a complicated area, it may be set to acquire an image at every partitioned road where the service user moves.

The information transmission unit 130" transfers the images related to the store and information related to the store, stored in the history storage unit 120", to the navigation service providing device 200".

The data reception unit 140" receives the navigation information transferred from the navigation service providing device 200". At this point, the data reception unit 140" further receives the digital contents transferred from the contents providing server 300", and the display unit 150" may display the digital contents received by the data reception unit 140" on the screen.

The display unit 150" displays the navigation information received by the data reception unit 140" on the screen. For example, when the navigation information is displayed on a smart glass, this is executed in an augmented reality mode, and the navigation information can be displayed using an image of an actual distance as is, and if the digital contents can be received furthermore, the digital contents can be displayed to be overlapped in a corresponding screen of the augmented realty mode in real-time.

Figure 21:
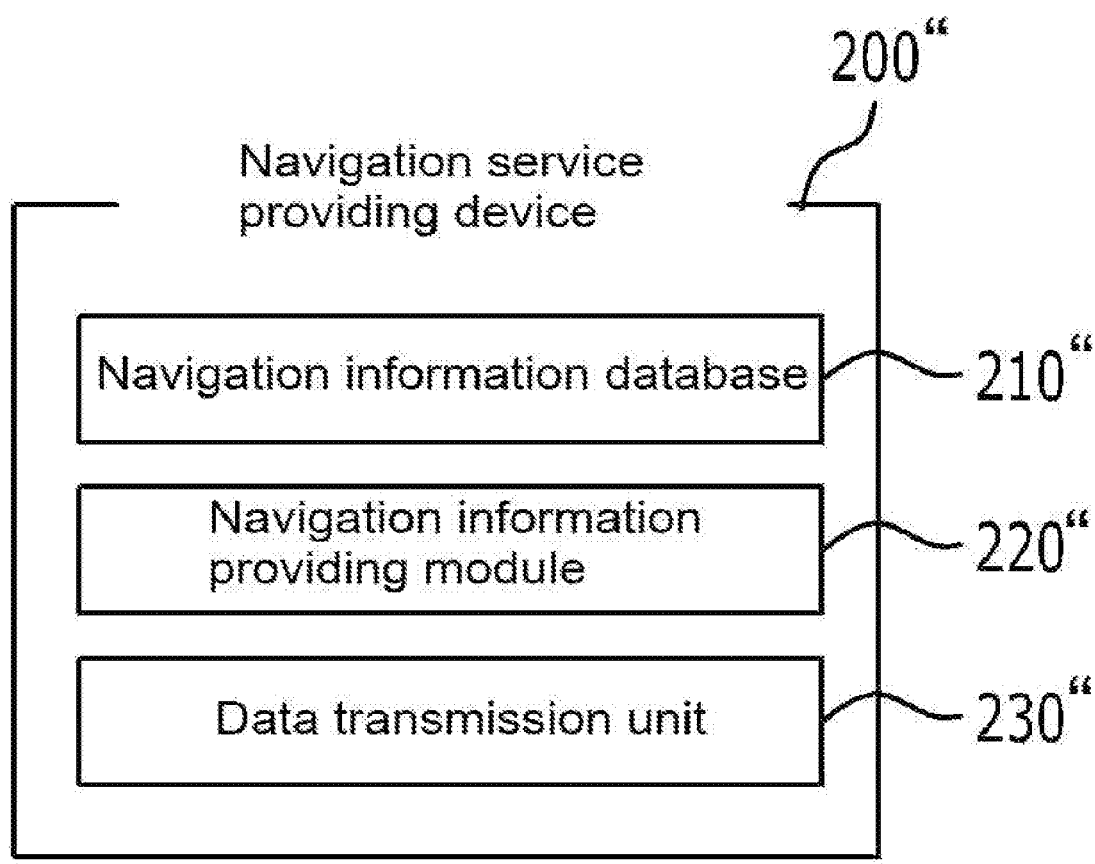
FIG. 21 is a block diagram showing the configuration of a navigation service providing device according to an embodiment of the present invention.

FIG. 21 is a block diagram showing the configuration of a navigation service providing device 200" according to an embodiment of the present invention.

The navigation service providing device 200" according to an embodiment of the present invention includes a data reception unit, a navigation information database 210", a navigation information providing module 220" and a data transmission unit 230". More specifically, the navigation service providing device 200" includes a data reception unit for receiving images related to visiting a store and information related to the store from one or more wearable devices 100" of users; a navigation information database 210" for storing the images related to visiting a store and the information related to the store, transferred from the data reception unit; a navigation information providing module 220" for providing navigation information selected using the images related to visiting a store and the information related to the store, transferred from the navigation information database 210"; and a data transmission unit 230" for transferring the navigation information provided by the navigation information providing module 220" to the wearable device 100".

The data reception unit receives images related to visiting a store and information related to the store needed to provide a navigation service, from one or more wearable devices 100" of users.

The navigation information database 210" stores the images related to visiting a store and the information related to the store, transferred from the data reception unit. At this point, the navigation information database 210" may store images related to visiting a store and information related to the store acquired by a plurality of users using the service.

The navigation information providing module 220" provides navigation information selected using the images related to visiting a store and the information related to the store, transferred from the navigation information database 210".

Figure 22:
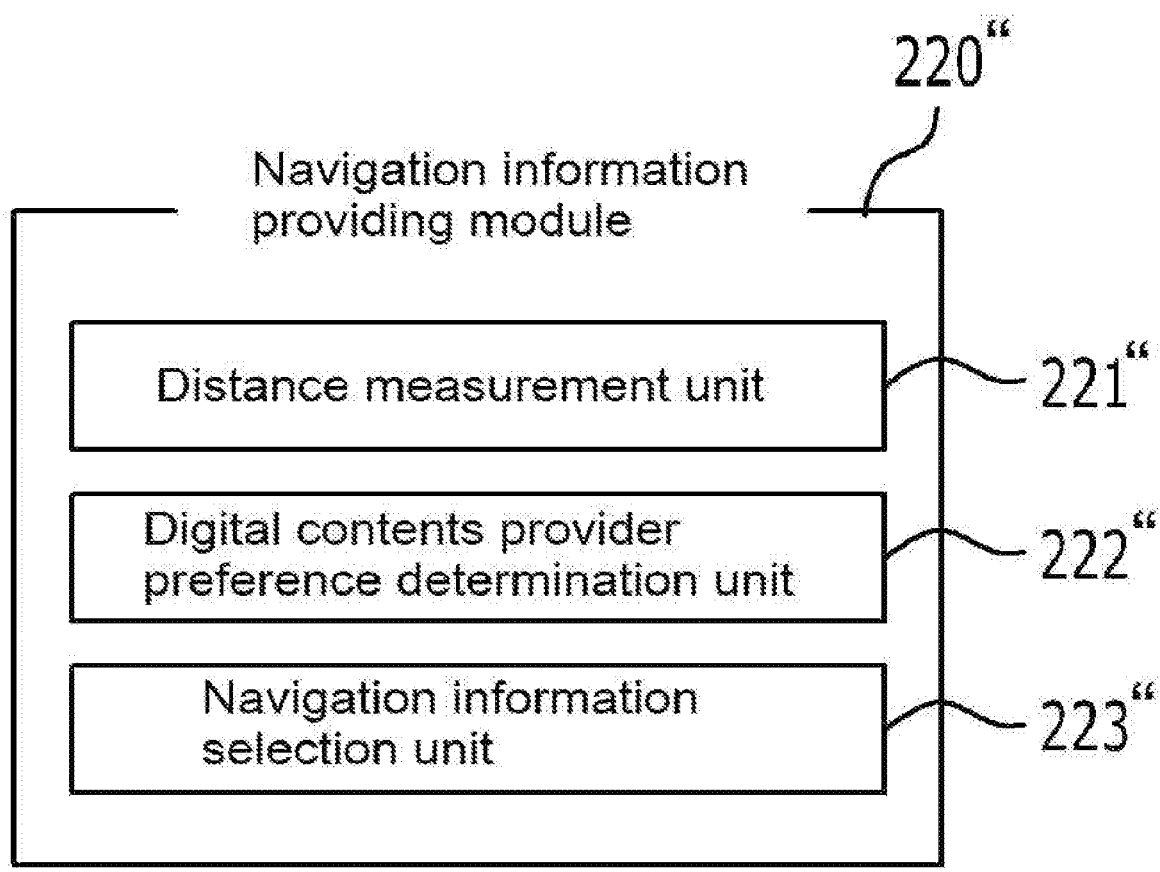
FIG. 22 is a block diagram showing the configuration of a navigation information providing module according to an embodiment of the present invention.

At this point, referring to FIG. 22, the navigation information providing module 220" may be configured of a distance measurement unit 221", a digital contents provider preference determination unit 222" and a navigation information selection unit 223". More specifically, the navigation information providing module 220" may include a distance measurement unit 221" for measuring a distance to the store, which is the object of the visit, using the information related to the store; a digital contents provider preference determination unit 222" for determining preference, of the digital contents provider providing digital contents, for the navigation service user; and a navigation information selection unit 223" for selecting and providing navigation information according to a preset priority.

The distance measurement unit 221" measures a distance to the store, which is the object of the visit, using the information related to the store. It measures, in real-time, information on the distance the service user has moved from the starting point to arrive at the destination.

The digital contents provider preference determination unit 222" determines preference, of the digital contents provider providing digital contents, for the navigation service user.

Meanwhile, the digital contents provider preference determination unit 222" may determine preference of the digital contents provider for the navigation service user considering at least any one of information among the number of using the digital contents provided by the digital contents provider by the navigation service user, whether or not the navigation service user agrees to provide position information, and a position of the navigation service user according to the provided position information if the navigation service user agrees to provide position information.

The navigation information selection unit 223" selects and provides navigation information according to a preset priority.

At this point, the information on the distance to the store to visit provided by the distance measurement unit 221" and the information on the preference for the navigation service user provided by the digital contents provider preference determination unit 222" can be simultaneously considered. For example, if the distance to the store to visit is within a preset distance, the navigation information selection unit may select navigation information according to the information on the preference for the navigation service user provided by the digital contents provider preference determination unit 222".

On the other hand, the navigation information selection unit may select navigation information by selecting any one of the information on the distance to the store to visit provided by the distance measurement unit 221" and the information on the preference for the navigation service user provided by the digital contents provider preference determination unit 222".

Like this, describing examples of alternatively selecting information, first, if the information on the distance to the store to visit provided by the distance measurement unit 221" is selected, the navigation information providing module may provide shortest distance navigation information for the store to visit, and at this point, shortest distance navigation information for the path actually used by users can be provided based on moved distance, moved time, information on the moving path, images photographed while moving, information related to the photographed images and the like of other users using the navigation service. At this point, if only the GPS information stored in the navigation service provider is utilized, the shortest distance navigation information may not be updated in some cases. For example, if the path is under construction or a real situation is not considered, the shortest path may not be provided. Accordingly, there are occasions in which guidance of road could be wrong although the user travels in a direction actually presented by displaying the navigation information on the display unit, and in this case, the user may select and move along a correct road based on the images photographed by other users while moving to the destination.

Second, if the information on the preference for the navigation service user provided by the digital contents provider preference determination unit 222" is selected, the navigation information providing module may provide navigation information for dropping in nearby stores which can provide digital contents provided by the digital contents provider. For example, although a service of guiding a path to a destination store is provided, this is providing navigation information for dropping in specific stores which can provide the contents provided by a platform company which provides the service or a service provider which provides the digital contents, without considering the shortest distance.

Since the digital contents are provided while a road is guided to drop in a specific store through the guidance service, the service user is persuaded to purchase a product or a service.

Meanwhile, the navigation information providing module 220" may further include an image combination performing unit for combining the navigation information with the images related to visiting a store.

At this point, the image combination performing unit may combine the images photographed by the wearable device 100" of the user in relation to visiting the store and stored in the navigation information database 210" with the images photographed by the wearable devices 100" of other users in relation to visiting the store. At this point, the image combination performing unit may provide images photographed at a place corresponding to the position information currently provided by the navigation information of the user, by utilizing position information contained in the information on the images photographed by other users.

Referring to FIG. 19, an image of a street is displayed in the upper right corner of the display of the wearable device 100" to be separate from the navigation information, and it may doubly confirm through the image whether or not the street corresponds to an area where the user actually passes through. This is conceived to solve the problem that the navigation information provided by a navigation service provider is generally updated after a predetermined period of time is elapsed, from the fact that the images acquired by the navigation service users in real-time can be immediately used. For example, if an image of a road guided by the navigation information corresponds to an image photographed by other users and displayed in the upper right corner, the user moves as is guided by the navigation information, and if the navigation information is information of a previous image, an image acquired while the service user himself or herself or other users move to a corresponding destination is confirmed in the upper right corner of the display unit 150" to be compared in real-time, and, at the same time, a further efficient moving path can be confirmed. At this point, the image may be a form of a picture or a short video.

The data transmission unit 230" transfers the navigation information provided by the navigation information providing module 220" to the wearable device 100". At this point, the data transmission unit 230" may further transfer navigation information provided by the navigation information providing module 220" to the contents providing server 300".

Figure 23:
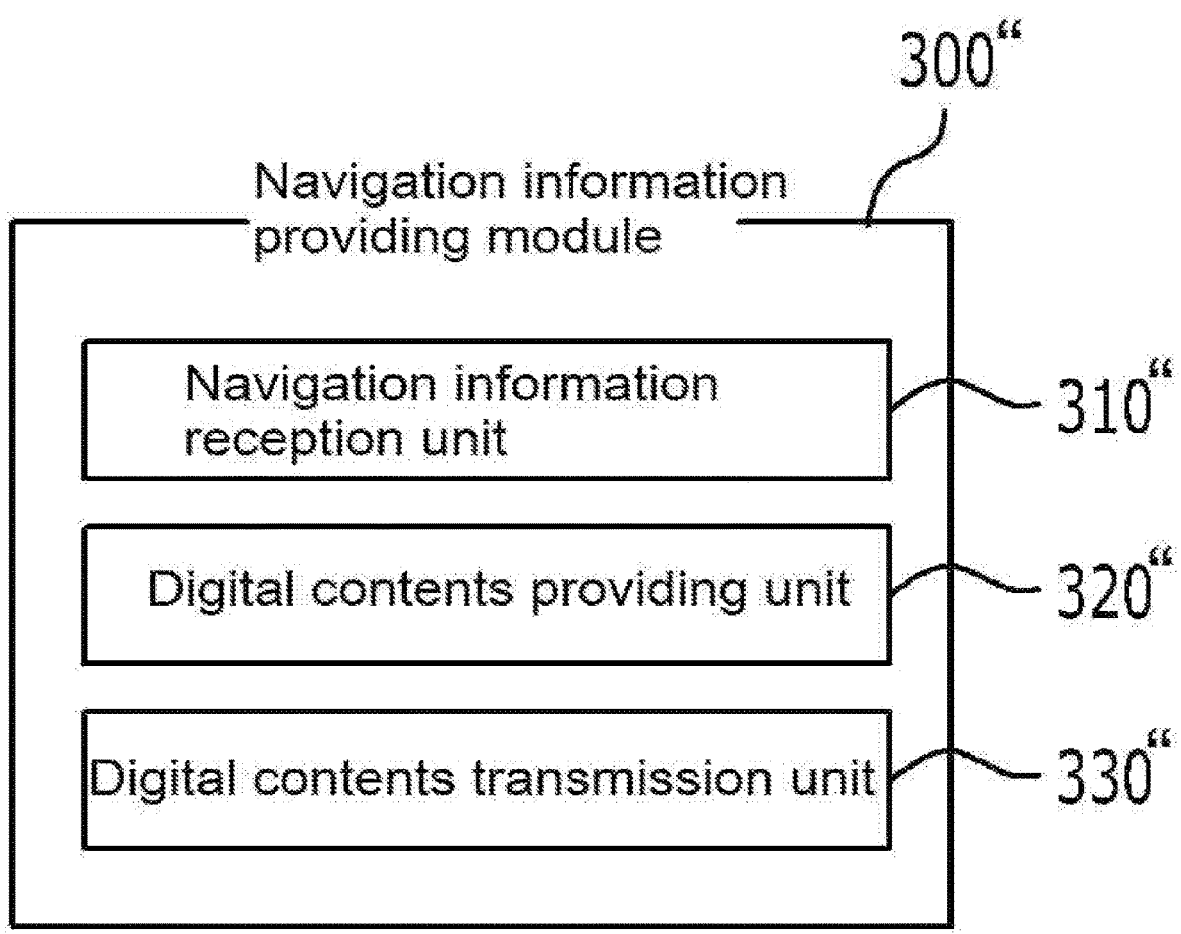
FIG. 23 is a block diagram showing the configuration of a contents providing server according to an embodiment of the present invention.

FIG. 23 is a block diagram showing the configuration of a contents providing server 300" according to an embodiment of the present invention.

The contents providing server 300" according to an embodiment of the present invention includes a navigation information reception unit 310", a digital contents providing unit 320" and a digital contents transmission unit 330".

More specifically, the contents providing server 300" includes a navigation information reception unit 310" for receiving navigation information from the navigation service providing device 200"; a digital contents providing unit 320" for transferring digital contents of a store recorded in the navigation information received by the navigation information reception unit 310" as a point to drop in or visit, to the digital contents transmission unit 330"; and a digital contents transmission unit 330" for transferring the digital contents transferred by the digital contents providing unit 320" to the wearable device 100".

The navigation information reception unit 310" receives navigation information for providing appropriate digital contents to a service user from the navigation service providing device 200". The received navigation information means navigation information containing information on the latest interested products transmitted from the service user in real-time.

The digital contents providing unit 320" transfers digital contents of a store recorded in the navigation information received by the navigation information reception unit 310" as a point to drop in or visit, to the digital contents transmission unit 330". The digital contents providing unit 320" may transfer a list of coupons that can be provided by a digital contents server to the digital contents transmission unit 330" based on the information.

The digital contents transmission unit 330" transfers the digital contents transferred by the digital contents providing unit 320" to the wearable device 100".

On the other hand, the contents providing server 300" may further include an authentication information transmission unit 130" for transferring authentication information to the membership connection device 400" to confirm whether or not a user holds membership of an affiliated company or a navigation service provider related to the digital contents transferred by the digital contents providing unit 320" to the wearable device 100".

At this point, the phone number and the name of the user, details of the provided contents and other diverse information can be used as the authentication information.

Figure 24:
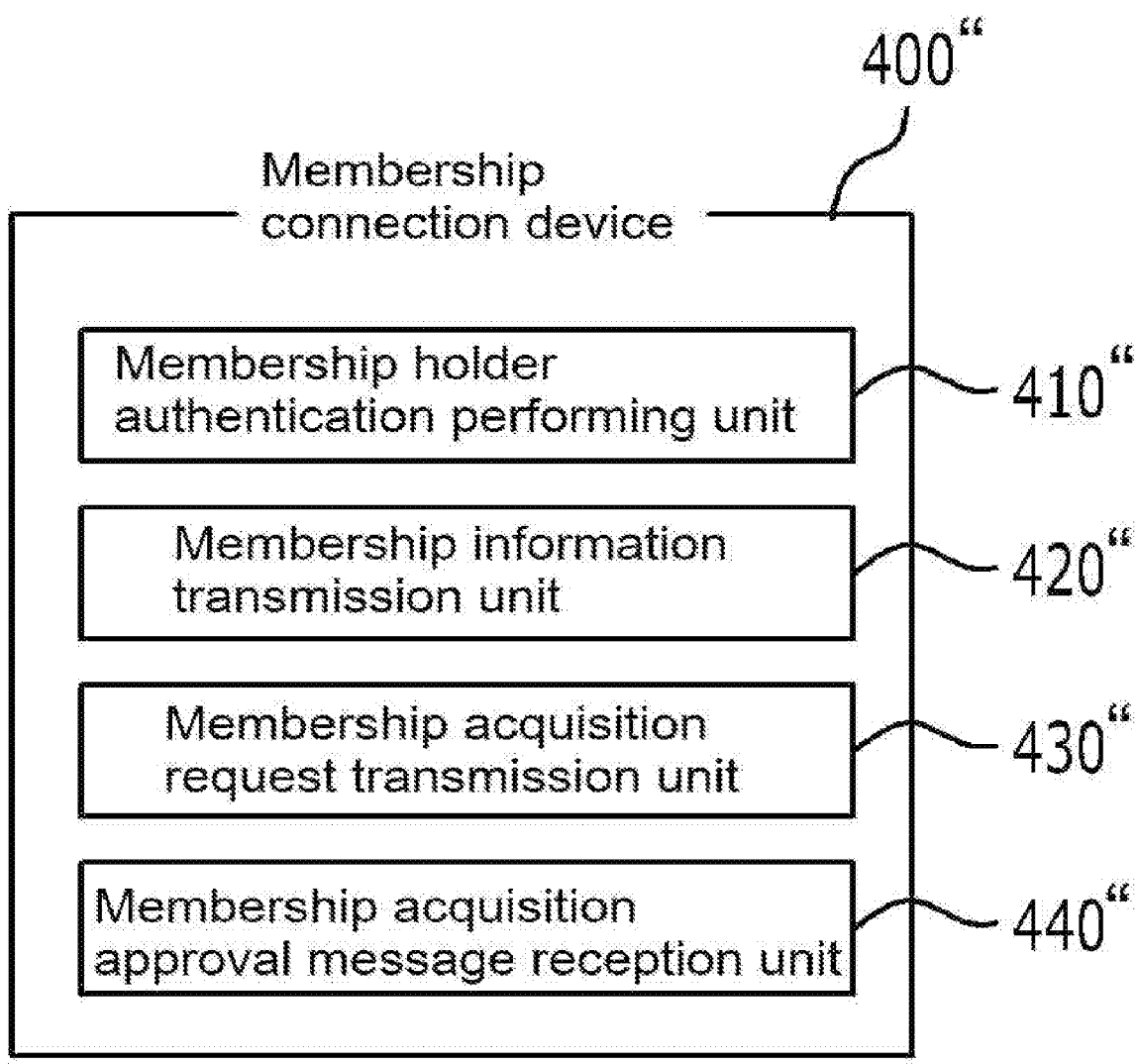
FIG. 24 is a block diagram showing the configuration of a membership connection device according to an embodiment of the present invention.

FIG. 24 is a block diagram showing the configuration of a membership connection device according to an embodiment of the present invention.

The membership connection device according to an embodiment of the present invention includes a membership holder authentication performing unit 410", a membership information transmission unit 420", a membership acquisition request transmission unit 430" and a membership acquisition approval message reception unit 440".

More specifically, the membership connection device a membership holder authentication performing unit 410" for performing authentication according to authentication information transferred from the contents providing server 300"; a membership information transmission unit 420" for transferring membership information of a user to the contents providing server 300" if it is confirmed that the user is a membership holder as a result of the authentication of the membership holder authentication performing unit; a membership acquisition request transmission unit 430" for transmitting a membership acquisition request message to the wearable device 100" if it is confirmed that the user is not a membership holder as a result of the authentication of the membership holder authentication performing unit; and a membership acquisition approval message reception unit 440" for receiving a membership acquisition approval message transmitted from the wearable device 100" in response to the membership acquisition request message.

The membership information transmission unit 420" transfers membership information of the user to the contents providing server 300" if it is confirmed that the user is a membership holder as a result of the authentication of the membership holder authentication performing unit. If the membership information transmission unit 420" transfers the membership information to the contents providing server 300", the contents providing server 300" may obtain a right for transferring digital contents (coupons) to the service user. Through the process like this, an effect of persuading a navigation service user to subscribe a service of an affiliated company which provides corresponding digital contents (coupons) is generated.

If it is confirmed that the user is not a membership holder as a result of the authentication of the membership holder authentication performing unit, the membership acquisition request transmission unit 430" transmits a membership acquisition request message to the wearable device 100".

The membership acquisition approval message reception unit 440" receives a membership acquisition approval message transmitted from the wearable device 100" in response to the membership acquisition request message.

Meanwhile, in the present invention, the membership connection device 400" is a device (a server) for inducing acquisition of membership, which is a configuration that can be further included by the need of a navigation service provider or a platform provider.

Figure 25:
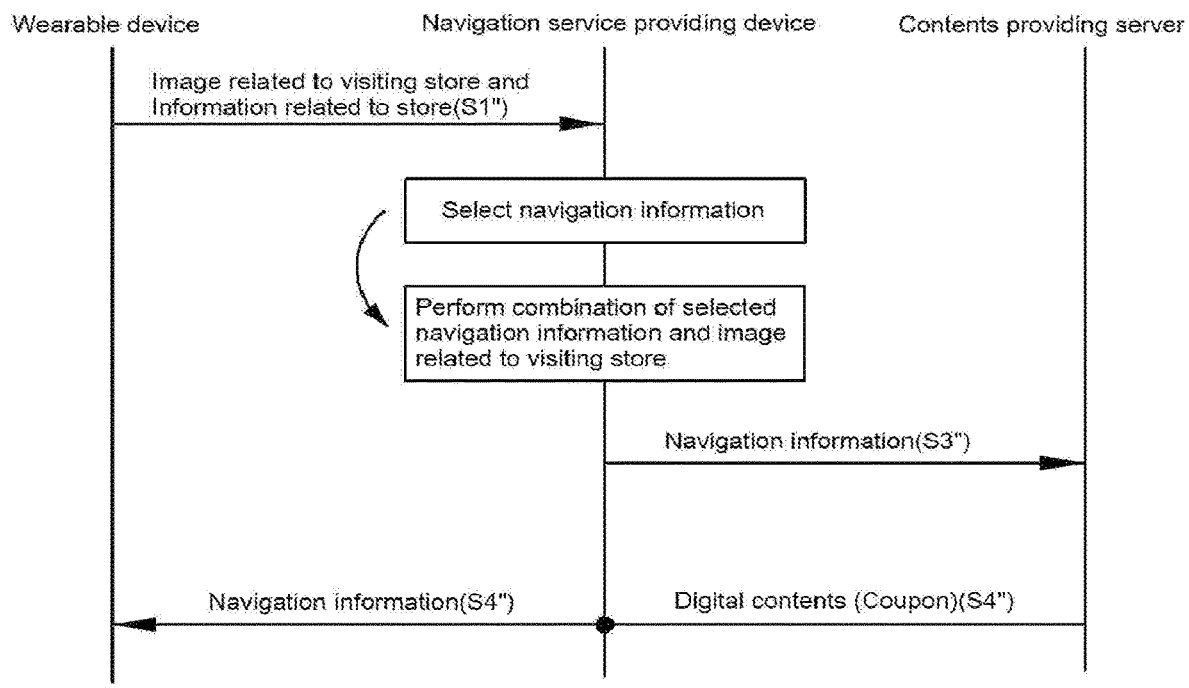
FIG. 25 is a view showing a method of providing a navigation service using a wearable device according to an embodiment of the present invention.

FIG. 25 is a view showing a method of providing a navigation service using a wearable device 100" according to an embodiment of the present invention.

A method of providing a navigation service by the navigation service providing system according to an embodiment of the present invention includes the steps of (1) transferring, by the wearable device 100", images related to visiting a store and information related to the store to the navigation service providing device 200" (step S1"); (2) selecting, by the navigation service providing device 200", navigation information using the images related to visiting a store and the information related to the store, transferred at step (1) (step S2"); (3) combining, by the navigation service providing device 200", the navigation information selected at step (2) with the images related to visiting a store (step S3"); (4) transferring, by the navigation service providing device 200", the navigation information combined with the images related to visiting a store at step (3) to the contents providing device 300" or the wearable device 100" (step S4"); and (5) receiving, by the contents providing device 300" or the wearable device 100", the navigation information combined with the images related to visiting a store (step S5").

Figure 26:
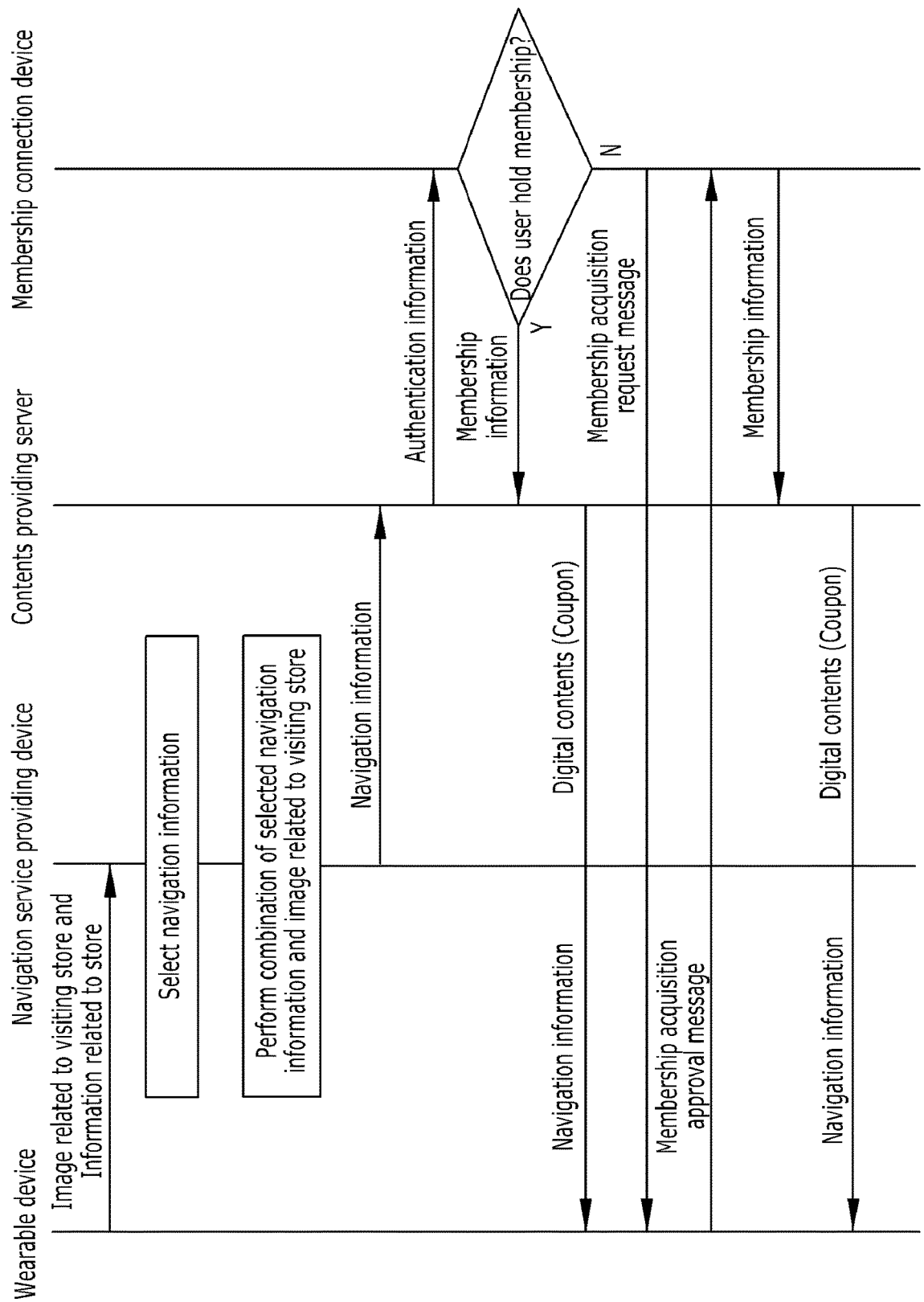
FIG. 26 is a sequence chart showing a method of providing a navigation service by performing authentication using a membership connection device according to another embodiment of the present invention.

Meanwhile, referring to FIG. 26, the method of providing a navigation service may further include the steps of, after step (2) and before step (3), (a) confirming, by the membership connection device 400" at step (2), whether or not a user holds membership of an affiliated company which provides digital contents using authentication information of a service user using the navigation service; (b) transferring, by the membership connection device 400", membership information of the user to the contents providing server 300" if it is confirmed that the user is a membership holder at step (a) and transferring a membership acquisition request message to the contents providing server 300" and the wearable device 100" if it is confirmed that the user is not a membership holder at step (a); and (c) transferring the membership information of the user to the contents providing server 300" if a membership acquisition approval message is transferred from the wearable device 100" in response to the membership acquisition request message transferred at step (b).

A method of providing a navigation service by the wearable device 100" according to an embodiment of the present invention includes the steps of (1) photographing images related to visiting a store while moving to the store, which is the object of the visit; (2) storing the images related to visiting a store photographed at step (1) and information related to the store; (3) transferring the images related to the store and the information related to the store stored at step (2) to the navigation service providing device 200"; (4) receiving the navigation information transferred at step (3); and (5) displaying the navigation information received at step (4) on the screen.

Meanwhile, the method of providing a navigation service may further receive digital contents transferred by the contents providing server 300" at step (4) and display the digital contents received at step (4) on the screen together with the navigation information.

A method of providing a navigation service by the navigation service providing device 200" according to an embodiment of the present invention includes (1) a data reception step of receiving images related to visiting a store and information related to the store from one or more wearable devices 100" of users; (2) a navigation information storage step of storing the images related to visiting a store and the information related to the store transferred at step (1); (3) a navigation information providing step of providing navigation information selected using the images related to visiting a store and the information related to the store transferred at step (2); and (4) a data transmission step of transferring the navigation information provided at step (3) to the wearable device 100".

At this point, step (3) may include the steps of (a) measuring a distance to the store, which is the object of the visit, and determining preference, of a digital contents provider providing digital contents, for the navigation service user; (b) selecting and providing navigation information according to a preset priority; and (c) combining the navigation information selected at step (b) with the images related to visiting a store.

At this point, at step (a), the digital contents provider preference determination unit 222" may determine preference of the digital contents provider for the navigation service user considering at least any one of information among the number of using the digital contents provided by the digital contents provider by the navigation service user, whether or not the navigation service user agrees to provide position information, and a position of the navigation service user according to the provided position information if the navigation service user agrees to provide position information.

At this point, at step (b), the navigation information can be selected by simultaneously using information on the distance to the store to visit and information on the preference for the navigation service user, measured at step (a). For example, if the measured distance to the store to visit is within a preset distance, the navigation information can be selected according to the information on the preference for the navigation service user provided by at step (a).

In addition, at step (b), the navigation information can be determined by selecting any one of the information on the distance to the store to visit and the information on the preference for the navigation service user provided at step (a), and if the information on the distance to the store to visit is selected, shortest distance navigation information for the store to visit is provided, and if the information on the preference for the navigation service user is selected, navigation information for dropping in nearby stores, which can provide digital contents provided by the digital contents provider, can be provided.

Meanwhile, at step (c), the images photographed by the wearable device 100" of the user in relation to visiting the store can be combined with the images photographed by the wearable devices 100" of other users in relation to visiting the store.

A method of providing a navigation service by the contents providing server 300" according to an embodiment of the present invention includes (1) a navigation information reception step of receiving navigation information from the navigation service providing device 200"; (2) a digital contents providing step of transferring digital contents of a store recorded in the navigation information received at step (1) as a point to drop in or visit, to the digital contents transmission unit 330"; and (3) a digital contents transmission step of transferring the digital contents transferred at step (2) to the wearable device 100".

Meanwhile, after step (2) and before step (3), the method of providing a navigation service may further include an authentication information transmission step of transferring authentication information to the membership connection device 400" to confirm whether or not a user holds membership of an affiliated company or a navigation service provider related to the digital contents.

A method of providing a navigation service by the membership connection device according to an embodiment of the present invention includes (1) a membership holder authentication performing step of performing authentication according to authentication information transferred from the contents providing server 300"; (2) a step of transferring membership information of a user to the contents providing server 300" if it is confirmed that the user is a membership holder as a result of the authentication at step (1) and transmitting a membership acquisition request message to the wearable device 100" if it is confirmed that the user is not a membership holder; and (3) a membership acquisition approval message receiving step of receiving a membership acquisition approval message transmitted from the wearable device 100" in response to the membership acquisition request message transmitted at step (2).

As described above, according to the present invention, since images related to a destination and information on the destination are collected using a wearable device 100" and navigation information is provided using the collected information, a user may swiftly and correctly move to the destination, and a service associated with digital contents can be provided in real-time using the information included in the navigation information.

In addition, an optimum moving path can be provided to a current navigation service user by using actual moving paths to a store to visit provided by navigation service users, and a moving path which can provide marketing information to the current navigation service user can be provided using the preference, of a service provider providing a navigation service, for the user.

Such a service providing method using a navigation service providing system can be created as a computer program, and codes and code segments constituting the computer program may be easily reasoned by a programmer in the art. In addition, the program related to the service providing method using a navigation service providing system is stored in an information storage medium that can be read by an electronic device and can be read and executed by the electronic device.

Like this, those skilled in the art may recognize that the present invention can be embodied in other specific forms without departing from the spirit and essential characteristics of the present invention. Therefore, it should be understood that the embodiments described above are illustrative and not restrictive to limit the scope. In addition, the flowcharts in the figures show sequential orders exemplarily shown to achieve the most desirable results in implementing the present invention, and it is apparent that other additional steps can be provided or some steps can be deleted.

Technical features described in this specification and implementations executing the features can be implemented in digital electronic circuitry, or in computer software, firmware or hardware including the structures disclosed in this specification and their structural equivalents, or in combinations of one or more of them. In addition, the implementations executing the features described in this specification can be implemented as one or more computer program products, i.e., one or more modules of computer program instructions encoded on a tangible program carrier for execution by, or to control the operation of, a data processing device.

A computer-readable medium can be a machine-readable storage device, a machine-readable storage substrate, a memory device, a composition of matter effecting a machine-readable propagated signal, or any combination thereof.

The term "device" or "system" in the specification encompasses all instruments, devices and machines for processing data, including a processor, a computer or multiple processors or computers. The processing system may include, in addition to hardware, a code that creates an execution environment for the computer program if requested, e.g., a code constituting processor firmware, a protocol stack, a database management system, an operating system, or any combination thereof.

A computer program also referred to as a program, software, a software application, a script or a code can be written in any form of programming language including compiled or interpreted languages, or declarative or procedural languages, and can be implemented in any form including as a standalone program or a module, a component, a subroutine or other units suitable for use in a computing environment.

Meanwhile, a computer program does not necessarily correspond to a file in a file system. A program can be stored in a single file or multiple coordinated files (e.g., files that store one or more modules, sub-programs, or portions of a code) provided in the requested program or in a portion of a file that holds other programs or data (e.g., one or more scripts stored in a markup language document).

A computer program can be implemented to be executed on multiple computers or one or more computers located at one site or distributed across multiple sites and interconnected by a wired/wireless communication network.

Meanwhile, the computer-readable media suitable for storing computer programs, instructions and data may include all forms of non-volatile memory, media and memory devices including by way of example semiconductor memory devices, e.g., EPROM, EEPROM, and flash memory devices; magnetic disks, e.g., internal hard disks or external disks; magneto-optical disks; and CD and DVD disks. Further, the processor and memory can be supplemented by, or incorporated in, special purpose logic circuitry.

The implementations executing the features described in this specification can be implemented in a computing system that includes a back end component, e.g., a data server, or that includes a middleware component, e.g., an application server, or that includes a front end component, e.g., a client computer having a Web browser or a graphical user interface through which a user can interact with an implementation of the subject matter described in this specification, or any combination of one or more of the back end, middleware or front end components. The components of the system can be interconnected by any form or medium of digital data communication, e.g., a communication network.

Hereinafter, a further specific embodiment for implementing configurations including the system described in this specification together with the above-described contents and an MO (mobile originated) service-based benefic providing method will be described in detail.

The system and the service providing method using a navigation service providing system described in this specification may be partially or entirely used through a means executing computer software, program codes or instructions on a server related to a client device or a web-based storage system or one or more processors included in the server. Here, the processor may be part of a computing platform such as a server, a client, a network infrastructure, a mobile computing platform, a fixed computing platform or the like, and specifically, it can be a kind of a computer or a processing device which can execute program instructions, codes or the like. In addition, the processor may further include memory for storing a service providing method using a navigation service providing system, instructions, codes and programs, and if the memory is not included, the processor may access, through a separate interface, a storage device such as a CD-ROM, a DVD, memory, a hard disk, a flash drive, RAM, ROM cache or the like in which the service providing method using a navigation service providing system, instructions, codes and programs are stored.

In addition, the system and the service providing method using a navigation service providing system described in this specification may be partially or entirely used through a machine that executes computer software on a server, a client, a gateway, a hub, a router or network hardware. The software may be executed in various kinds of servers such as a file server, a print server, a domain server, an Internet server, an Intranet server, a host server, a distributed server and the like, and the servers may further include memories, processors, computer-readable storage media, storage media, communication devices, ports, clients and interfaces capable of accessing other servers through a wired/wireless network.

The service providing method using a navigation service providing system, instructions, codes and the like also can be executed by a server, and other devices required for execution of the service providing method using a navigation service providing system can be implemented as a part of a hierarchical structure associated with the server.

In addition, the server may provide an interface to other devices including, without limitation, clients, other servers, printers, database servers, print servers, file servers, communication servers, distributed servers and the like, and a connection through the interface may facilitate remote execution of a program through a wired/wireless network.

In addition, any one of the devices attached to the server through an interface may further include at least one storage device capable of storing a service providing system using a navigation service providing system, instructions, codes and the like, and the central processor of the server may provide the device with instructions, codes and the like to be executed on different devices to be stored in the storage device.

On the other hand, the system and the service providing method using a navigation service providing system described in this specification may be partially or entirely used through a network infrastructure. Here, the network infrastructure may include all of devices such as computing devices, servers, routers, hubs, firewalls, clients, personal computers, communication devices, routing devices and the like, separate modules capable of executing each of the functions and the like and may further include a storage medium such as flash memory, a buffer, a stack, RAM, ROM and the like in addition to the devices and modules mention above. In addition, the service providing method using a navigation service providing system, instructions, codes and the like also can be executed and stored by any one of the devices, modules and storage media included in the network infrastructure, and other devices needed to execute the service providing method using a navigation service providing system also can be implemented as a part of the network infrastructure.

In addition, the system and the service providing method using a navigation service providing system described in this specification may be implemented in hardware or a combination of hardware and software suitable for a particular application. Here, the hardware may include all of general purpose computer devices such as a personal computer, a mobile communication device and the like and specific computer devices for enterprise, and the computer device may be implemented as a device including memory, microprocessors, microcontrollers, digital signal processors, application integrated circuits, programmable gate arrays, programmable array organizations (→ logic) and the like or a combination thereof.

The computer software, instructions, program codes and the like described above may be stored or accessed by a readable device. Here, the readable device may include memory such as: computer components that retains digital data used for computing for some interval of time; semiconductor storage such as RAM or ROM; permanent storage such as optical disks; mass storage such as hard disks, tapes, drums or the like; optical storage such as CD or DVD; computer-detachable mass storage such as flash memory, floppy disks, magnetic tapes, paper tapes, standalone RAM disks or the like; network connection storage such as dynamic memory, static memory, variable storage or clouds, and the like. Meanwhile, although the instructions, codes or the like include all the languages including data-oriented languages (e.g., SQL, dBase), system languages (e.g., C, Objective-C, C++, Assembly), architectural languages (e.g., Java, .NET), and application languages (e.g., PHP, Ruby, Perl, Python), they are not limited thereto and include all other languages known to those of skill in the art.

In addition, the term "computer-readable medium" described in this specification includes all the media contributing to providing instructions for execution of a program to a processor. Specifically, the medium includes, but not limited to, non-volatile media such as data storage devices, optical disks, magnetic disks and the like, volatile media such as dynamic memory and the like, and transmission media such as coaxial cables, copper wires, fiber optics and the like for transmitting data.

Meanwhile, the elements executing the technical features of the present invention, which are included in the block diagrams and flowcharts shown in the drawings attached to this specification, imply logical boundaries between the elements.

However, according to software or hardware embodiments, since the depicted elements and the functions thereof may be executed in the form of a standalone software module, a monolithic software structure, a code, a service and a combination of these and stored in a medium executable in a computer provided with a processor capable of executing stored program codes, instructions and the like to implement their functions, all such implementations may be regarded as being included within the scope of the present invention.

Thus, while the attached drawings and descriptions thereof set forth technical features of the present invention, no particular arrangement of software for implementing these functional aspects should be inferred from these descriptions unless explicitly stated or otherwise clear from the context. That is, there may exist various embodiments described above, and since part of the embodiments can be modified while possessing technical features the same as those of the present invention, all the modifications should be regarded as being included within the scope of the present invention.

While operations are depicted in the drawings in a particular order, this is shown to achieve the most desirable results should not be understood as requiring that such operations should be performed in the particular order shown or in a sequential order or that all the illustrated operations should be performed. In certain circumstances, multitasking and parallel processing may be advantageous. Moreover, separation of various system components in the embodiments described above should not be understood as requiring such separation in all embodiments, and it should be understood that the described program components and systems can generally be integrated together in a single software product or packaged into multiple software products.

As described above, this specification is not intended to limit the present invention by the proposed specific terms. Accordingly, although the present invention has been described in detail with reference to the embodiments described above, those skilled in the art may make alterations, changes and modifications on the embodiments without departing from the scope of the present invention.

The scope of the present invention is represented by the claims to be described below rather than the detailed description, and it is to be interpreted that the meaning and scope of the claims and all the changes or modified forms derived from the equivalents thereof come within the scope of the present invention.

According to the present invention, since images related to a destination and information on the destination are collected using a wearable device and navigation information is provided using the collected information, a user may swiftly and correctly move to the destination, and thus the present invention has industrial applicability.

In addition, since a service associated with digital contents can be provided in real-time using the information included in the navigation information, an effect advantageous to marketing can be obtained, and thus the present invention has industrial applicability.

In addition, since an optimum moving path can be provided to a current navigation service user by using actual moving paths to a store to visit provided by navigation service users, the present invention has industrial applicability.

In addition, since a moving path which can provide marketing information to the current navigation service user can be provided using the preference, of a service provider providing a navigation service, for the user, the present invention has industrial applicability.

According to the present invention, since an estimated time of arrival at a destination according to an average walking speed of a user is provided using a wearable device, the user may arrive at the destination within the estimated time on foot.

In addition, since a taxi call service is recommended if the moving speed of the user is lower than a predetermined speed or too slow, the user may arrive at the destination within an estimated time.

In addition, if the moving speed of the user is lower than a predetermined speed or too slow, the reasons of delaying the walking can be understood and the health state of the user can be determined by measuring biometric information of the user.

Another object of the present invention is to provide a service associated with digital contents in real-time using navigation information.

Still another object of the present invention is to provide an optimum moving path to a current navigation service user by utilizing attribute information of products to be purchased by navigation service users.

Still another object of the present invention is to provide a shortest moving path using locations of products to be purchased by navigation service users.

According to the present invention, since images related to a destination and information on the destination are collected using a wearable device and navigation information is provided using the collected information, a user may visually confirm a road with ease and move to the destination.

In addition, since a service associated with digital contents is provided in real-time using the information included in the navigation information, benefits such as digital contents (coupons) or the like can be provided to a service user.

In addition, there is an effect of providing an optimum moving path to a current navigation service user by using actual moving paths to a store to visit provided by navigation service users.

In addition, since a moving path which can provide marketing information to the current navigation service user can be provided using the preference, of a service provider providing a navigation service, for the user, there is an advantageous effect in marketing.

The effects of the present invention are not limited to the effects mentioned above, and various effects can be included within the scope clearly understood by those skilled in the art from the above descriptions.

What is claimed is:

1. A method of providing a walking path guidance service, comprising:
   measuring a motion and position information of a user;
   calculating a speed information using the measured motion and position information of the user;
   creating a walking path from a starting point to a destination and calculating a time of arrival at the destination of the walking path according to the speed; and
   calculating, when a movement according to the walking path is sensed, a moving speed using the motion and recommending a vehicle call service if a predetermined condition is satisfied.

2. The method according to claim 1, wherein the measuring the motion and position information measures biometric information of the user, and if the calculated moving speed is lower than a preset threshold speed, whether or not the user is in a normal condition is determined by comparing the biometric information with previously stored reference biometric information.

3. The method according to claim 1, further comprising storing map information.

4. A navigation service providing method comprising:
   receiving current position information of a user and an interested product list data from a wearable device;
   providing navigation information of the interested product list data using in-store product information; and
   transferring the navigation information data to the wearable device,
   wherein the providing navigation information includes:
   extracting product information of interested products recorded in the interested product list;
   creating shortest distance information by analyzing positions of at least one or more interested products using position information among the information on the interested products;
   creating navigation information using product attribute information among the information on the interested products; and
   selecting and providing navigation information according to a preset priority.

5. The method according to claim 4, wherein the product attribute information includes at least any one of information on a category, a quantity and a weight of a product.

6. The method according to claim 4, wherein the selecting and providing navigation information selects the navigation information by simultaneously considering the shortest distance information and the product attribute navigation information.

7. The method according to claim 4, wherein the selecting and providing navigation information selects the navigation information by simultaneously considering any one of the shortest distance information and the product attribute navigation information.

8. The method according to claim 4, wherein the transferring the navigation information further transfers the navigation information data to a contents providing server.

9. A navigation service providing method comprising:
   receiving images related to visiting a store and information related to the store from one or more wearable devices of users;
   storing the images related to visiting a store and the information related to the store;
   providing navigation information generated using the images related to visiting a store and the information related to the store; and
   transferring the navigation information to the wearable device,
   wherein the images related to visiting the store comprises images of places photographed every preset time or every preset distance while moving to the store,
   wherein the information related to the store comprises at least one of position information of a place where the images related to visiting the store are photographed and path information used to move to the store from a place where the images related to visiting the store are photographed.

10. The method according to claim 9, wherein the providing the navigation information includes measuring a distance to the store, which is an object of the visit, using the information related to the store.

11. The method according to claim 10, wherein the providing the navigation information provides shortest distance navigation information for the store to visit using the information on the distance to the store to visit.

12. The method according to claim 9, wherein the providing the navigation information further includes determining preference, of a digital contents provider providing digital contents, for a navigation service user.

13. The method according to claim 12, wherein the providing the navigation information provides navigation information for dropping in nearby stores which can provide digital contents provided by the digital contents provider, using information on the preference for the navigation service user.

14. The method according to claim 12, further comprising selecting and providing navigation information according to a preset priority.

15. The method according to claim 14, wherein the selecting and providing the navigation information selects the navigation information using at least one of information on a distance to a store to visit and information on the preference for the navigation service user.

16. The method according to claim 12, wherein the determining the preference determines the preference of the digital contents provider for the navigation service user considering at least any one of information among the number of using the digital contents provided by the digital contents provider by the navigation service user, whether or not the navigation service user agrees to provide position information, and a position of the navigation service user according to the provided position information if the navigation service user agrees to provide position information.

17. The method according to claim 9, wherein the providing the navigation information includes combining the navigation information with the images related to visiting a store.

* * * * *